(12) United States Patent
Buluwela et al.

(10) Patent No.: US 7,202,025 B1
(45) Date of Patent: Apr. 10, 2007

(54) CONTROL OF GENE EXPRESSION

(75) Inventors: Lakjaya Buluwela, London (GB); Simak Ali, London (GB)

(73) Assignee: Gene Expression Technologies Limited, London (GB)

( * ) Notice: Subject to any disclaimer, the term of this patent is extended or adjusted under 35 U.S.C. 154(b) by 402 days.

(21) Appl. No.: 10/019,520

(22) PCT Filed: Jun. 28, 2000

(86) PCT No.: PCT/GB00/02497

§ 371 (c)(1),
(2), (4) Date: Jun. 10, 2002

(87) PCT Pub. No.: WO01/02019

PCT Pub. Date: Jan. 11, 2001

(30) Foreign Application Priority Data

Jun. 30, 1999 (GB) ................. 9915126.8

(51) Int. Cl.
C12Q 1/68 (2006.01)
C12N 15/63 (2006.01)
G01N 33/53 (2006.01)
G01N 33/566 (2006.01)
C07H 21/04 (2006.01)

(52) U.S. Cl. .................. 435/6; 435/7.1; 435/91.1; 435/455; 436/501; 536/23.1; 536/23.4; 536/24.1; 536/24.5

(58) Field of Classification Search .................. 435/6, 435/91.1, 455, 7.1; 536/23.1, 25.3, 24.1, 536/23.4, 24.5; 530/300, 350; 514/1, 2; 424/9.1; 436/501
See application file for complete search history.

(56) References Cited

FOREIGN PATENT DOCUMENTS

| WO | WO 96/06166 | 2/1996 |
|----|-------------|--------|
| WO | WO 98/53057 | 11/1998 |
| WO | WO 98/54311 | 12/1998 |
| WO | WO 99/02683 | 1/1999 |
| WO | WO 99/23885 | 5/1999 |
| WO | WO 00/41566 | 7/2000 |
| WO | WO 00/42219 | 7/2000 |
| WO | WO 00/73434 A1 | 12/2000 |
| WO | WO 01/00815 A1 | 1/2001 |

OTHER PUBLICATIONS

Pooga, M. et al., FASEB J., vol. 12, pp. 67-77 (1998).*
Elliot, G. et al., Cell, vol. 88, pp. 223-233 (1997).*
Derossi, D., J. Biol. Chem., vol. 269, No. 14, pp. 10,444-10450 (1994).*
Grignani, F. et al., Nature, vol. 391, pp. 815-818 (1998).*
Chien, P.-Y., et al., Molecular Endocrinology, vol. 13, No. 12, pp. 1161-1167 (1998).*

Grignani et al, NATURE, *Fusion Proteins of the Retinoic Acid receptor-a Recuit Histone Deacetylase in Promyelocytic Leukaemia*, vol. 391, Feb. 19, 1998, pp. 815-818.
Kevin Struhl, Genes & Development, *Histone acetylation and Transcriptional Regulatory Mechanisms*, 1998, 12:599-606.
Beerli et al, National Academy of Sciences, *Toward Controlling Gene Expression at Will: Specific Regulation of the erbB-2/HER-2 Promotor by Using Polydactyl Zinc Finger Proteins Constructed From Modular Building Blocks*, 1998, pp. 14628-14633.
Hsieh et al, National Academy of Sciences, *CIR, a Corepressor Linking the DNA binding factor CBF1 to the Histone Deacetylase Complex*, pp. 23-28.
Chien et al, Molecular Endocrinology, *A Fusion Protein of the Estrogen Receptor (ER) and Nuclear Receptor Corepressor (NcoR) Strongly Inhibits Estrogen-Dependent Responses in Breast Cancer Cells*, vol. 13, No. 12, 1999, pp. 2122-2136.
Chen et al, EMBO Journal, *Fusion Between a Novel Kruppel-Like Zinc Finger Gene and the Retinoic Acid Receptor-a Locus Due to a Variant t (11;17) Translocation Associated with Acute Promyelocytic Leukaemia*, vol. 12 No. 13, 1993, pp. 1161-1167.
Grozinger et al, National Academy of Sciences, *Three Proteins Define a Class of Human Histone Deacetylases Related to Yeast Hdalp*, vol. 96, Apr. 1999 pp. 4868-4873.
Guidez et al, BLOOD, *Reduced Retinoic Acid-Sensitive of Nuclear Receptor Corepressor Binding to PML- and PLZF-RARa Underlie Molecular Pathogenesis and Treatment of Acute Promyelocytic Leukemia*, vol. 91, Apr. 15, 1998, pp. 2634-2642.
Tora et al, EMBO Journal, *The Cloned Human Oestrogen Receptor Contains a Mutation Which Alters its Hormone Binding Properties*, vol. 8, No. 7, pp. 1981-1986, 1989.
Tilley et al, National Academy of Sciences, *Characterization and Expression of a cDNA Encoding the Human Androgen Receptor*, vol. 86, Jan. 1989, pp. 327-331.
Aharon Razin, EMBO Journal, *CpG Methylation, Chromatin Sructure and Gene Silencing-a Three-Way Connection*, vol 17, 1998, pp. 4905-4908.
David et al, ONCOGENE, *Histone Deacetylase Associated with mSin3A Mediates Repression by the Acute Promyelocytic Leukemia-Associated PLZF Protein*, (1998), 16, pp. 2549-2556.
Lin et al, NATURE, *Role of the Histone Deacetylase Complex in Acute Promyelocytic Leukaemia*, vol. 391, Feb. 19, 1998, pp. 811-814.
Horlein et al, NATURE, *Ligand-Independent Repression by the Thyroid Hormone Receptor Mediated by a Nuclear Receptor Co-Repressor*, vol. 377, Oct. 5, 1995, pp. 397-405.
Chen and Li, Critical Reviews, *Coactivation and Corepression in Transcriptional Regulation by Steroid/Nuclear Hormone Receptors*, 8 (2), 1998, pp. 169-190.
Workman and Kingston, Annu. Rev. Biochem., *Alteration of Nucleosome Structure as a Mechanism of Transcriptional Regulation*, 1998, 67:545-79.

(Continued)

*Primary Examiner*—Jane Zara
(74) *Attorney, Agent, or Firm*—Nikolai & Mersereau, P.A.; C. G. Mersereau

(57) ABSTRACT

A method of suppressing the expression of a selected gene in a eukaryotic cell the method comprising introducing into the cell (a) a polypeptide comprising a DNA binding portion which binds to a site at or associated with the selected gene which site is present in a plant r animal genome and a chromatin inactivation portion, or (b) a polynucleotide encoding said polypeptide.

4 Claims, 5 Drawing Sheets

OTHER PUBLICATIONS

Perlmann and Vennstrom, NATURE, *The Sound of Silence*, vol. 377, Oct. 5, 1995, pp. 387-389.

Wolffe, NATURE, *Sinful Repression*, vol. 387, May 1, 1997, pp. 16-17.

Grunstein et al, NATURE, *Histone Acetylation in Chromatin Structure and Transcription*, Sep. 25, 1997, vol. 389 pp. 349-353.

Pazin and Kadonaga, CELL, *What's Up and Down With Histone Deacetylation and Transcription*, vol. 89, May 2, 1997, pp. 325-328.

DePinho, NATURE, *The Cancer-Chromatin Connection*, vol. 391, Feb. 5, 1998, pp. 532-537.

Bestor, NATURE, *Methylation Meets Acetylation*, vol. 393, May 28, 1998, pp. 311-313.

Grunstein, CELL, *Yeast Heterochromatin: Regulation of Its Assembly and Inheritance by Histones*, vol. 93, May 1, 1998, pp. 325-328.

Margolin, National Academy Sciences, *Kruppel-Associated Boxes are Potent Transcriptional Repression Domains*, vol. 91 May 1994, pp. 4509-4513.

Schultz et al, Genes and Development, *Targeting Histone Deacetylase Complexes via KRAB-Zinc Finger Proteins: The PHD and Bromodomains of KAP-1 Form a Cooperative Unit That Recruits a Novel Isoform of the MI-2A Subunit of NURD*, 2001, 15:428-443.

Kim et al, Proc. National Academy Sciences, *A Novel Member of the Ring Finger Family, KRIP-1, Associates With the KRAB-A Transcriptional Repressor Domain of Zinc Finger Proteins*, vol. 93, Dec. 1996, pp. 15299-15304.

Lin et al, Biochemical and Biophysical Research Communications, *Catonic Liposome-mediated Incorporation of Prostatic Acid Phosphatase Protein Into Human Prostate Carcinoma Cells*, vol. 192, No. 2, 1993, pp. 413-419.

Chu et al, Pharmaceutical Research, *Efficiency of Cytoplasmic Delivery by pH-Sensitive Liposomes to Cells in Culture*, vol. 7, No. 8, 1990, pp. 824-834.

Lindgren et al, Trends in Pharmacological Science, *Cell-penetrating Peptides*, vol. 21, 2000, pp. 99-103.

Jacek Hawiger, Current Opinion in Chemical Biology, *Noninvasive Intracellular Delivery of Functional Peptides and Proteins*, vol. 3, 1999, pp. 89-84.

\* cited by examiner

Annex 1: Figures

Figure 3
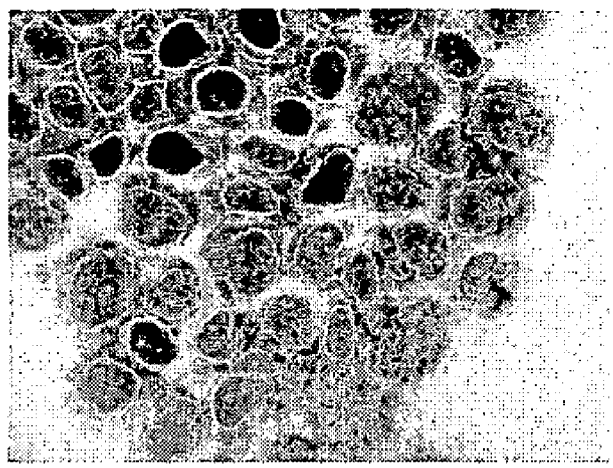
A
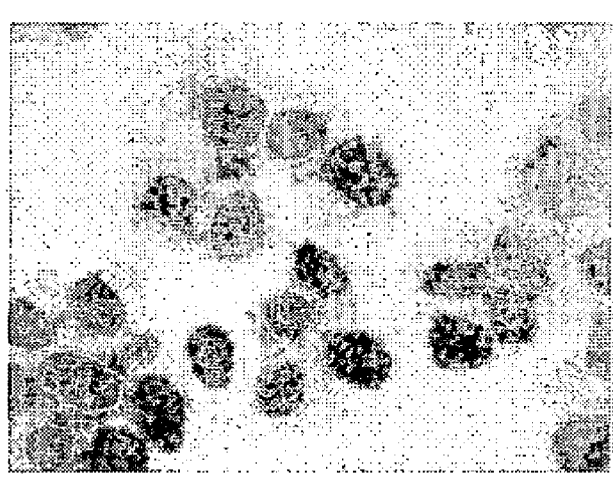
B
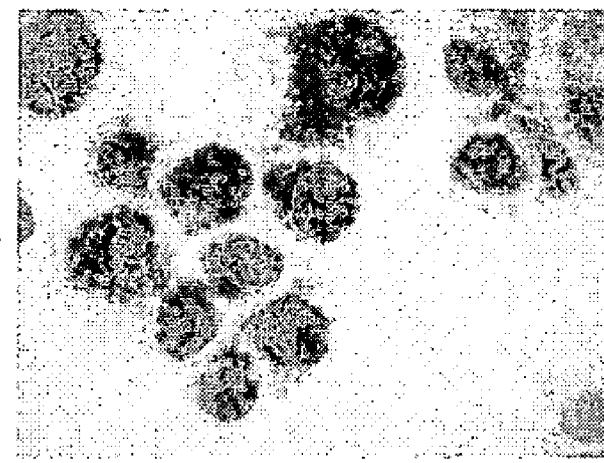
C

Figure 5

Alignment of the Amino Acid Sequences Encoding HDAC1 from Man, Plant and Yeast

```
Human HD1        M-------AQTQGTRRKVCYYYDGDVGNYYYGQGHPMKPHRIRMTHNLLLNYGLYRKMEIYRPHKANAEEMTKYHSDDYIKFLRSIRPDNMSEYSKQ
Arabidopsis HD   MDTGGNSLA--SGPDGVKRKVCYFYDPEVGNYYYGQGHPMKPHRIRMTHALLAHYGLLQHMQVLKPFPARERDLCRFHADDYVSFLRSITPETQQDIRQ
Yeast HD1        MVYEATPFDPITVKPSDKRRVAYFYDADVGNYAYGAGHPMKPHRIRMKAHSLIMNYGLYKKMEIYRAKPATKQEMCQFHTDEYIDFLSRVTPDNLEMFKRE
                     .       .   . .  *  **.**** * ****** .**  **.* ::* *** :::**** *  :   .*: : .**:.: *     . *:

Human HD1        MQRFNVGEDCPVFDGLFEFCQLSTGGSVASAVKLNKQQTDIAVNWAGGLHHAKKSEASGFCYVNDIVLAILELLKYHQRVLYIDIDIHHGDGVEEAFYTT
Arabidopsis HD   LKRFNVGEDCPVFDGLYSFCQTYAGGSVGGSVKLNHGLCDIAINWAGGLHHAKKCEASGFCYVNDIVLAILELLKKQHERVLYVDIDIHHGDGVEEAFYAT
Yeast HD1        SVKFNVGDDCPVFDGLYEYCSISGGGSMEGAARLNRGKCDVAVNYAGGLHHAKKSEASGFCYLNDIVLGIIELLRYHPRVLYIDIDVHHGDGVEEAFYTT
                  ::*****:****** . *.: :*** ..:  ** .  .** *::***********.*******:***** *:***: * ****:***:********:*

Human HD1        DRVMTVSFHKYGEYFPGTGDLRDIGAGKGKYYAVNYPLRDGIDDESYEAIFKPVMSKVMEMFQPSAVVLQCGSDSLSGDRLGCFNLTIKGHAKCVEFVKS
Arabidopsis HD   DRVMTVSFHKFGDYFPGTGHIQDIGYGSGKYYSLNVPLDDGIDDESYHLLFKPIMGKVMEIFRPGAVVLQCGADSLSGDRLGCFNLSIKGHAECVKFMRS
Yeast HD1        DRVMTCSFHKYGEFFPGTGELRDIGVGAGKNYAVNVPLRDGIDDATYRSVFEPVIKKIMEWYQPSAVVLQCGGDSLSGDRLGCFNLSMEGHANCVNYVKS
                 ***** ****:*::*****.::*** *.**:*::*.**.****: * : *:*:  :** :: .*******.**********:: *** **:  :*

Human HD1        FNLPMLMLGGGGYTIRNVARCWTYETAVALDTEIPNELPYNDYFEYFGPDFKLHISPSNMTNQNTNEYLEKIKQRLFENLRMLPHAPGVQMQAIPEDAIP
Arabidopsis HD   FNVPLLLLGGGGYTIRNVARCWCYETGVALGVEVEDKMPEHEYYEYFGPDYTLHVAPSNMENKNSRQMLEEIRNDLLHNLSKLQHAPSVPFQERPPDTET
Yeast HD1        FGIPMRVVGGGGYTMRNVARTWCFETGLLNNVVLDKDLPYNEYYEYYGPDYKLSVRPSNMFNVNTPEYLDKVMTNIFANLENTKYAPSVQLNHTPRDA--
                 * :*: :******:*****.* :**.:   . :  :  *::*:**:***: * :.***** ::* .: *:::::::. **.   :** *   .

Human HD1        EESGDEDED-----DPDKRISICSSDKRIAC--EEEFSDSEEEGEGGRKNSSNFKKAKRVKTEDEKEKDPEEKEVTEEKT--KEEKPEAKGVKEEVKLA
Arabidopsis HD   PEVDEDQEDGDKRWDPDSDMDVDDDRKPIPSRVKREAVEPDTKDKDGLKGIMERGKGCEVEVDESGSTKVTGVNPVGVEEASVKMEEEGTNKGGAEQAFPPKT
Yeast HD1        EDLGDVEED-----SAEAK-----------------------------------DTKGGSQYARDLHVEHDNEFY
                   :.* :*                                                    .    : *:::
```

CONTROL OF GENE EXPRESSION

The present application is the U.S. national stage of co-pending PCT International Application No. PCT/GB00/02497, having an International filing date of Jun. 28, 2000, and having a priority date of Jun. 30, 1999 and entitled: CONTROL OF GENE EXPRESSION.

BACKGROUND OF THE INVENTION

1. Field of the Invention

The present invention relates to the control of gene expression and, in particular, it relates to methods of, and means for, suppressing the expression of a particular, selected gene.

2. Related Art

The ability to selectively suppress the expression of a gene is useful in many areas of biology, for example in methods of treatment where the expression of the gene may be undesirable; in preparing models of disease where lack of expression of a particular gene is associated with the disease; in modifying the phenotype in order to produce desirable properties. Thus, the ability to selectively suppress the expression of a gene may allow the "knockout" of human genes in human cells (whether wild type or mutant) and the knockout of eukaryotic genes in studies of development and differentiation.

Present methods of attempting to suppress the expression of a particular gene fall into three main categories, namely antisense technology, ribozyme technology and targeted gene deletion brought about by homologous recombination.

Antisense techniques rely on the introduction of a nucleic acid molecule into a cell which typically is complementary to a mRNA expressed by the selected gene. The antisense molecule typically suppresses translation of the mRNA molecule and prevents the expression of the polypeptide encoded by the gene. Modifications of the antisense technique may prevent the transcription of the selected gene by the antisense molecule binding to the gene's DNA to form a triple helix.

Ribozyme techniques rely on the introduction of a nucleic acid molecule into a cell which expresses a RNA molecule which binds to, and catalyses the selective cleavage of, a target RNA molecule. The target RNA molecule is typically a mRNA molecule, but it may be, for example, a retroviral RNA molecule.

Antisense- and ribozyme-based techniques have proven difficult to implement and they show varying degrees of success in target gene suppression or inactivation. Furthermore, these two techniques require persistent expression or administration of the gene-inactivating agent.

Targeted gene deletion by homologous recombination requires two gene-inactivating events (one for each allele) and is not easily applicable to primary cells, particularly for example primary human mammary cells which can only be maintained in culture for a few passages. Targeted gene deletion has remained difficult to perform in plants. The cre-lox mediated site-specific integration has been the method of choice although the efficiency of specific integrative events is low (Alberts et al (1995) *Plant J.* 7, 649–659; Vergunst & Hooykass (1998) *Plant Mol. Biol.* 38, 393–406; Vergunst et al (1998) *Nucl. Acids Res.* 26, 2729–2734).

These major shortcomings in existing technology have led us to seek an alternative strategy.

Acute promyelocytic leukaemia (APL) is underlined by the involvement of mutant retinoic acid receptor (RAR) proteins, formed by gene fusions brought about by chromosomal translocations. Molecular analysis of one APL subset has identified a fusion between the RARα gene and a Kruppel-like zinc finger gene named promyelocytic leukaemia zinc finger (PLZF). Further investigations have shown that the resulting PLZF-RARα fusion protein functions as a gene repressor by targeting histone deacetylation of retinoic acid regulated genes. Several studies have shown that this repression is mediated by the PLZF portion of the fusion protein, which interacts with a complex of proteins which includes the components N-CoR, SMRT, Sin3 and HDAC and which in turn results in the recruitment of the histone deacetylase (HDAC) complex to target genes (see, for example, Grignani et al (1998) *Nature* 391, 815–818; Chen et al (1993) *EMBO J.* 12, 1161–1167; Razin (1998) *EMBO J.* 17, 4905–4908; David et al (1998) *Oncogene* 16, 2549–2556; and Lin et al (1998) *Nature* 391, 811–814). HDAC directed gene inactivation, therefore results from the targeted assembly of components, some of which have been identified (eg N-CoR, SMRT, Sin3 etc) making a gene inactivating complex which mediates its effect through histone deacetylation.

Although this work shows that in certain forms of APL fusion proteins are able to recruit histone deacetylase activity which appears to have the effect of inactivating the expression of certain genes, no-one has suggested that a method can be devised based on recruitment of histone deacetylase or other means of inactivating chromatin in order to selectively suppress expression of a chosen target gene or a set of genes. Surprisingly, we have shown that this can be achieved.

RARα-PLZF and RARα-PML fusion proteins are known from studies of acute promyelocytic leukaemia (APL) and are described in, for example, Grignani et al (1998) *Nature* 391, 815–818.

Fusions of GAL4 with a portion of PLZF protein, and LexA DNA binding domain fused to various fragment of Sin 3A are described in David et al (1998) *Oncogene* 16, 2549–2556 which, for the avoidance of doubt, are excluded from the polypeptide of the present invention. Fusions of the GAL4 DNA binding domain and PLZF-RARα are described in Lin et al (1998) *Nature* 391, 811–814 which, for the avoidance of doubt, are excluded from the polypeptide of the present invention.

Fusions of the GAL4 DNA binding domain with N-CoR or portions thereof, or with the C terminal domain of the T$_3$Rβ1 receptor molecule (thyroid hormone receptor molecule), and LexA DNA binding domain fused with the C terminal domain of the T$_3$Rα or RARα (retinoic acid receptor) receptor molecules, which, for the avoidance of doubt, are excluded from the polypeptide of the present invention, are described in Hörlein et al (1995) *Nature* 377, 397404. Fusions of the GAL4 DNA binding domain with the C terminal domain of vErbA (viral oncogene erbA of the avian erythroblastosis virus (AEV)), T$_3$R and RAR receptor molecules are also mentioned. These polypeptides are also, for the avoidance of doubt, excluded from the polypeptide of the present invention.

There is no suggestion in David et al (1998) *Oncogene* 16, 2549–2556, Lin et al (1998) *Nature* 391, 811–814 or Hörlein et al (1995) *Nature* 377, 397–404 that polypeptides comprising a nucleic acid binding portion and a chromatin inactivation portion can be designed and engineered to bring about the selective suppression of a chosen gene. Rather, David et al (1998) and Lin et al (1998) are both studies of gene repression in acute promyelocytic leukaemia, and Hörlein et al (1995) relates to the identification of N-CoR.

SUMMARY OF THE INVENTION

A first aspect of the invention provides a polypeptide comprising a nucleic acid binding portion which binds to a site present in a eukaryotic genome and a chromatin inactivation portion provided that when the nucleic acid binding portion is a DNA binding portion of RARα the chromatin inactivation portion is not a portion of PLZF protein and is not a portion of PML protein; and provided that when the nucleic acid binding portion is a DNA binding portion of the *Saccharomyces cerevisiae* GAL4 protein the chromatin inactivation portion is not a portion of PLZF protein, the C-terminal domain of vErbA, $T_3R$, $T_3R\beta1$ or RAR, or N-CoR or a portion of N-CoR; and provided that when the nucleic acid binding portion is a DNA binding portion of the *Escherichia coli* LexA the chromatin inactivation portion is not mSin3, or the C-terminal domain of $T_3R\alpha$ or RARα.

The polypeptides of the invention may be useful in methods and uses provided by further aspects of the invention, discussed in more detail below. In particular, the polypeptides of the invention may be useful in a method of suppressing the expression of a selected gene in a eukaryotic cell the method comprising introducing into the cell (a) a polypeptide comprising a nucleic acid binding portion which binds to a site at or associated with the selected gene which site is present in a eukaryotic genome and a chromatin inactivation portion, or (b) a polynucleotide encoding said polypeptide.

It is preferred if the polypeptides of the invention are hybrid polypeptides which do not occur in nature. For example, it is preferred if the nucleic acid binding portion is derived from one protein and that the chromatin inactivation portion is derived from a different protein and that the molecular configuration does not arise in nature, for example through chromosome translocation events. The proteins from which the nucleic acid binding portion and the chromatin inactivation portion are derived may be from the same species (for example, as is described in more detail below, the nucleic acid binding portion may be a DNA binding portion of a human steroid receptor protein such as oestrogen receptor (ER) and the chromatin inactivation portion may be a portion of human PLZF) or they may be from different species (for example a bacterial DNA binding protein may be fused to a portion of human PLZF).

Thus, in a particular preferred embodiment the polypeptide of the invention is one which is produced by genetic engineering means wherein the nucleic acid binding portion and the chromatin inactivation portion are selected as is described in more detail below.

It is preferred if the nucleic acid binding portion is not the *Saccharomyces cerevisiae* GAL4 protein or a DNA-binding portion thereof, and it is preferred if the nucleic acid binding portion is not the *Escherichia coli* LexA protein or a DNA-binding portion thereof.

In relation to the first aspect of the invention the site present in a eukaryotic genome is a site which is at or associated with a selected gene or genes whose expression it is desirable to suppress or inactivate. It is preferred if the site is a site which is naturally present in a eukaryotic genome. However, as is discussed in more detail below, the site may be one which has been engineered into the genome, or it may be a site associated with an inserted viral sequence. The site engineered into the genome to be in the vicinity of the gene whose expression is to be suppressed may be a site from the same species (but present elsewhere in the genome) or it may be a site present in a different species. By "genome" we include not only chromosomal DNA but other DNA present in the eukaryotic cell, such as DNA which has been introduced into the cell, for example plasmid or viral DNA. It is preferred if the nucleic acid binding portion can bind to chromosomal DNA or, as is described in more detail below, to RNA transcribed from chromosomal DNA.

The chromatin inactivation portion may be any polypeptide or part thereof which directly or indirectly leads to chromatin inactivation. By "directly" leading to chromatin inactivation we mean that the polypeptide or part thereof itself acts on the chromatin to inactivate it. By "indirectly" leading to chromatin inactivation we mean that the polypeptide or part thereof does not itself act on the chromatin but rather it is able to recruit or promote a cellular component to do so.

BRIEF DESCRIPTION OF THE DRAWINGS

FIGS. 3A and 3B represent a comparison of the in vitro DNA binding by wild-type human ERα and PLZF-ER;

FIG. 5 shows the alignment of the amino-acid sequence and coating HDAC1 from man, *arabidopsis* and yeast.

DETAILED DESCRIPTION

Figure 1:
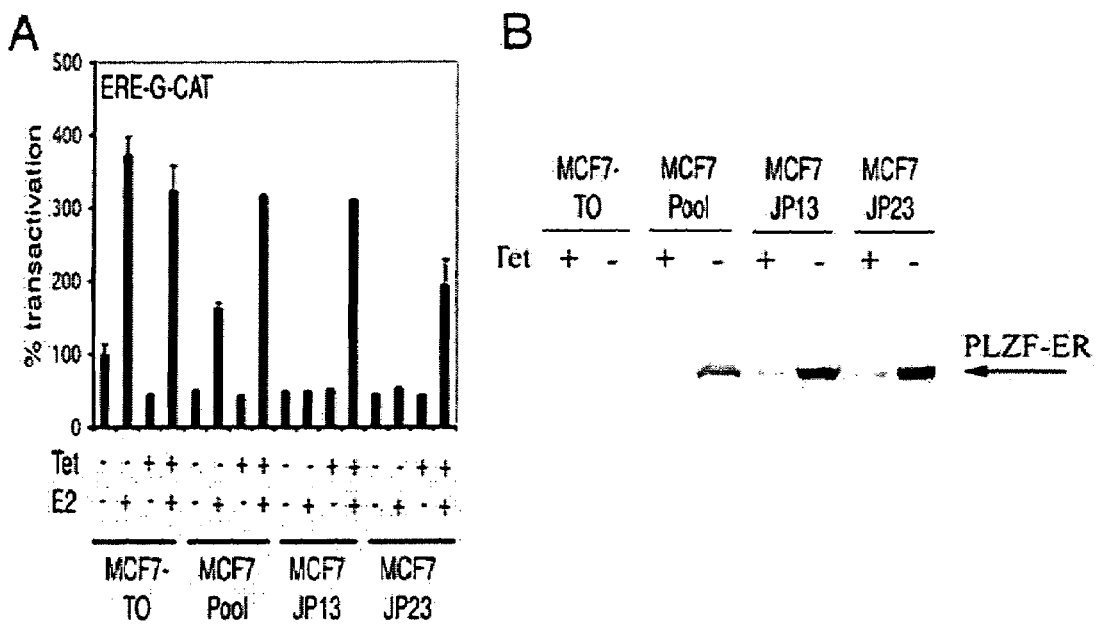
FIG. 1 shows a schematic representation of the HDAC complex.

Chromatin inactivation generally results in the suppression or inactivation of gene expression. Chromatin inactivation is typically a localised event such that suppression or inactivation of gene expression is restricted to, typically, one or a few genes. Thus, the chromatin inactivation portion is any suitable polypeptide which, when part of the polypeptide of the invention and when targeted to a selected gene by the nucleic acid binding portion, locally inactivates the chromatin associated with the selected gene so that expression of the gene is inactivated or suppressed. Histone deacetylation is associated with chromatin inactivation and so it is particularly preferred if the chromatin inactivation portion facilitates histone deacetylation. Targeted deacetylation of histones associated with a given gene leads to gene inactivation in an, essentially, irreversible manner. By "suppression" or "inactivation" of gene expression we mean that in the presence of the polypeptide of the invention the expression of the selected, targeted gene is at least five-fold, preferably at least ten-fold, more preferably at least 100-fold, and most preferably at least 1000-fold lower than in the absence of the polypeptide of the invention under equivalent conditions. Gene expression can be measured using any suitable method including using reverse transcriptase-polymerase chain reaction (RT-PCR), RNA hybridisation, RNAse protection assays, nuclear run-off assays and alteration of chromatin as judged by DNAse 1 hypersensitivity.

In animal and plant cells histone deacetylation is brought about by the so-called histone deacetylase complex (HDAC) which contains, in addition to one or more histone deacetylase enzymes, ancillary proteins which are involved in the formation and function of the complex. In addition, there are other protein components which although they may not be part of HDAC they bind to or otherwise interact with HDAC and help facilitate histone deacetylation.

Deacetylation and acetylation of histones is a well-known phenomenon which is reviewed in the following: Chen & Li (1998) *Crit. Rev. Eukaryotic Gene Expression* 8, 169–190; Workman & Kingston (1998) *Ann. Rev. Biochem.* 67, 545–579; Perlmann & Vennstrom (1995) *Nature* 377, 387-; Wolfe (1997) *Nature* 387, 1617; Grunstein (1997) *Nature* 389, 349–352; Pazin & Kadonaga (1997) *Cell* 89, 325–328; DePinho (1998) *Nature* 391, 533–536; Bestor (1998) *Nature* 393, 311–312; and Grunstein (1998) *Cell* 93, 325–328.

The polypeptide composition of the HDAC complex is currently under investigation. Polypeptides which may form part of, or are associated with, certain HDAC complexes include histone deacetylase 1 (HDAC1) Taunton et al (1996) *Nature* 272, 408–441); histone deacetylase 2 (HDAC2) (Yang et al (1996) *Proc. Natl. Acad. Sci. USA* 93, 12845–12850); histone deacetylase 3 (HDAC3) (Dangond et al (1998) *Biochem. Biophys. Res. Comm.* 242, 648–652); N-CoR (Horlein et al (1995) *Nature* 377, 397–404); SMRT (Chen & Evans (1995) *Nature* 377, 454–457); SAP30 (Zhang et al (1998) *Molecular Cell* 1, 1021–1031). Sin3 (Ayer et al (1995) *Cell* 80, 767–776; Schreiber-Agus et al (1995) *Cell* 80, 777–786) SAP18 (Zhang et al (1997) *Cell* 89, 357–364); and RbAp48 (Qian et al (1993) *Nature* 364, 648–652). All of these papers are incorporated herein by reference. It is believed that there may be further components of the HDAC complex or which interact with the HDAC complex which are, as yet, undiscovered. It is envisaged that these too will be useful in the practice of the invention.

PLZF has been shown to interact with N-CoR and SMRT, which in turn recruit a HDAC complex. PLZF will also directly interact with HDAC (Lin et al (1998) *Nature* 391, 811–814; Grignani et al (1998) *Nature* 391, 815–818; David et al (1998) *Oncogene* 16, 2549–2556). Complexes formed which contain any of N-CoR, SMRT, Sin3, SAP18, SAP30 and histone deacetylase are described in Heinzel et al (1997) *Nature* 387, 4348; Alland et al (1997) *Nature* 387, 49–55; Hassig et al (1997) *Cell* 89, 341–347; Laherty et al (1997) *Cell* 89, 349–356; Zhang et al (1997) *Cell* 89, 357–364; Kadosh & Struhl (1997) *Cell* 89, 365–371; Nagy et al (1997) *Cell* 89, 373–380; and Laherty et al (1998) *Molecular Cell* 2, 3342. All of these papers are incorporated herein by reference.

Thus, it is particularly preferred if the component of a HDAC complex or the polypeptide which binds to or facilitates recruitment of a HDAC complex is any one of PLZF, SMRT, Sin3, SAP18, SAP30 or N-CoR, or HDACs including HDAC1, HDAC2 or HDAC3. It will be appreciated that it may not be necessary for all of the polypeptides to be present so long as a functional portion thereof is present. For example, with respect to histone deacetylase enzymes (for example, HDAC1, HDAC2 or HDAC3) the functional portion may be a portion that retains histone deacetylase activity or it may be a portion which contains a binding site for other components of a HDAC complex or a portion which otherwise recruits the HDAC complex and promotes histone deacetylation. Similarly, with respect to other components of the HDAC complex or polypeptides which bind to the HDAC complex the functional portion may be a portion which contains a binding site for other components of the HDAC complex. To date six mammalian HDAC genes have been described (Grozinger et al (1999) *Proc. Natl. Acad. Sci. USA* 96, 4868–4873), it is believed that any one or more of these may be useful in the practise of the present invention.

It is preferred that the chromatin inactivation portion is not N-CoR or a portion thereof; or the C-terminal domain of the vErbA, $T_3R$ (including $T_3R\beta1$ or $T_3R\alpha$) or RAR (including RAR$\alpha$) receptor molecule, particularly if the nucleic acid binding portion is the *Saccharomyces cerevisiae* GAL4 protein or a DNA-binding portion thereof, or the *Escherichia coli* LexA protein or a DNA-binding portion thereof.

It is believed that binding motifs are present within the components of the HDAC complex or within polypeptides which bind the HDAC complex and these motifs may be sufficient to act as chromatin inactivation portions in the polypeptide of the invention since they may facilitate histone deacetylation by recruiting a HDAC complex.

Furthermore, it will be appreciated that variants of a component of the HDAC complex or variants of a polypeptide which binds to the HDAC complex may be used. Suitable variants include not only functional portions as described above, but also variants in which amino acid residues have been deleted or replaced or inserted provided that the variant is still able to facilitate histone deacetylation. Thus, suitable variants include variants of histone deacetylase in which the amino acid sequence has been modified compared to wild-type but which retain their ability to deacetylate histones. Similarly, suitable variants include variants of, for example, Sin3 or PLZF in which the amino acid sequence has been modified compared to wild-type but which retain their ability to interact with or in the HDAC complex. Similarly, variants of other proteins interacting with components of the HDAC complex and other transcription factors that can bring about gene inactivation through HDAC activity may be used.

All or parts of the Rb, MAD and MeCpG2 proteins may interact with the HDAC complex.

While most work has been done on HDAC complexes and polypeptides involved in recruiting HDAC complexes in mammalian systems, the fundamental nature of the system is such that functionally equivalent polypeptides are expected to be found in other eukaryotic cells, in particular in other animal cells and in plant cells. For example, FIG. 5 shows that polypeptides very closely related to human HDAC1 are present in *arabidopsis* and in yeast. A plant HDAC complex has been isolated from maize (Lussen et al (1997) *Science* 277, 88–91) and a comparative study of histone deacetylases from plant, fungal and vertebrate cells has been undertaken (Lechner et al (1996) *Biochim. Biophys. Acta* 1296, 181 –188). Histone deacetylase inhibitors have been shown to derepress silent rRNA genes in *Brassica* (Chen & Pickard (1997) *Genes Dev.* 11, 2124–2136) and a naturally occurring host selective toxin (HC toxin) from *Cochliobolus carbonum* inhibits plant, fungal and mammalian histone deacetylases (Brosch et al (1995) *Plant Cell* 7, 1941–1950).

It is not necessary that the chromatin inactivation portion is from the same cell type or species as the cell into which the polypeptide (or polynucleotide encoding the polypeptide) is introduced but it is desirable if it is since such a chromatin inactivation portion may be able to inactivate chromatin more effectively in that cell.

It is particularly preferred if the chromatin inactivation portion of the polypeptide is PLZF, a portion of PLZF that can facilitate histone deacetylation, or a polypeptide, or portion of a polypeptide, known to cause gene activation via histone deacetylation. For example, the portion of PLZF in PLZF-RAR$\alpha$ which is involved in APL is believed to interact with N-CoR and SMRT.

It is also particularly preferred if the chromatin inactivation portion is a polypeptide with histone deacetylase enzyme activity such as contained in HDAC1, HDAC2 or HDAC3.

The nucleic acid binding portion may be any suitable binding portion which binds to a site present in a eukaryote, such as a plant or animal, genome. It is particularly preferred that the nucleic acid binding portion is able to bind to a site which is at or associated with a selected gene whose expression is to be suppressed by the presence of the chromatin inactivating portion of the polypeptide of the invention. It is preferred that the nucleic acid binding portion binds selectively to the desired site. There may be one or more desired sites to which the nucleic acid binding portion may bind. For example, the polypeptide of the invention may be used to suppress the expression of a group of genes which each have a binding site for a common DNA binding portion (for example, are under the controls of a steroid hormone receptor such as the oestrogen receptor (ER)). For the avoidance of doubt, the site present in the eukaryote may be a naturally occurring site, or it may be a site which has been engineered to be there. The site need not be originally from the same or any other eukaryote. For example, it may be a bacterial repressor binding site which has been engineered to be present in the DNA of the eukaryotic cell, or it may be a mammalian steroid hormone receptor binding site which has been engineered into plant cells. However, it is preferred if the site to which the nucleic acid binding portion binds is naturally present in the eukaryotic cell and is present in its natural position in the genome.

The nucleic acid binding portion may be a DNA binding portion or an RNA binding portion. Proteins which have the ability to bind either DNA or RNA in a sequence selective manner are well known in the art and some are described in more detail below. In the case of the RNA binding portion, the site present in the eukaryotic genome which binds the RNA binding portion is, typically, nascent RNA being transcribed from DNA at the selected site for inactivation. The RNA may be that which is being transcribed by the gene whose expression is to be suppressed, or it may be that which is being transcribed by a gene adjacent to, or at least close to, the gene whose expression is to be suppressed. It is preferred that the RNA binding portion binds to an RNA sequence which is at or close to the 5' end of the transcript. It will be appreciated that whilst being transcribed, nascent RNA remains at or close to its site of transcription and that if the site of transcription is at or close to the gene whose expression is to be suppressed, using an RNA binding portion in the polypeptide of the invention facilitates the localisation of the chromatin inactivation portion to the desired site.

The DNA binding portion may be all or a DNA-binding portion of a zinc-finger DNA binding protein or it may be all or a DNA-binding portion of a helix-turn-helix DNA binding protein.

Suitably the DNA binding portion may be all or a DNA-binding portion of an animal or plant DNA binding protein, or it may be all or a DNA binding portion of a bacterial or yeast DNA binding protein which has been engineered to bind to one or more sites in the plant or animal genome. Bacterial or yeast DNA binding proteins are less preferred and it is particularly preferred if the DNA binding protein does not contain a DNA binding portion of wild-type *Saccharomyces cerevisiae* GAL4 or wild-type *Escherichia coli* LexA.

Any DNA binding protein with the ability to bind DNA through a DNA recognition sequence may be used. This includes DNA binding proteins, and engineered DNA binding proteins, such as engineered zinc finger proteins and helix-turn-helix DNA binding proteins.

Databases listing transcription factors and their binding sites are listed below:

http://www.embl-heidelberg.de/srs5bin/cgi-bin/wgetz?-fun+pagelibinfo+-info+TFFACTOR http://www.embl-heidelberg.de/srs5bin/cgi-bin/wgetz?-fun+pagelibinfo+-info+TFSITE http://www.embl-heidelberg.de/srs5bin/cgi-bin/wgetz?-fun+pagelibinfo+-info+TFCELL http://www.embl-heidelberg.de/srs5bin/cgi-bin/wgetz?-fun+pagelibinof+-info+TFCLASS http://www.embl-heidelberg.de/srs5bin/cgi-bin/wgetz?-fun+pagelibinfo+-info+TFMATRIX http://www.embl-heidelberg.de/srs5bin/cgi-bin/wgetz?-fun+pagelibinfo+-info+TFGENE It is believed that all or part of the listed transcription factors may be useful in the practice of the invention.

Other gene regulatory proteins which may be useful in the practice of the invention include virally encoded DNA binding proteins such as those required for regulating viral and cellular gene expression and/or viral replication. These include but are not limited to the large T antigen of polyoma viruses, the E2 protein of papillomaviruses and the ICP4, ICP0 protein of herpesviruses.

Sequence specific RNA binding proteins, which bind to nascent RNA, may be engineered to bring about gene inactivation by the methods of the invention through HDAC complex formation in the proximity of transcriptionally active chromatin. For example, the transcriptionally active chromatin may be proviral and the RNA binding protein one which binds to transcribed proviral RNA. The tat protein of HIV is an example of an RNA binding protein.

In plants, DNA binding proteins are involved in, amongst other things, floral development, cold regulation/adaptation, and plant responses to ethylene or pathogens. Thus, the polypeptides of the invention, and the methods of the invention described below, may be used to analyse the role of these genes in these developmental and other processes.

A particularly preferred embodiment is wherein the DNA binding portion is all or a DNA binding part of a nuclear receptor DNA binding protein such as a steroid hormone receptor protein.

The nuclear receptor DNA binding protein superfamily includes oestrogen receptor (ER), androgen receptor (AR), progesterone receptor (PR), retinoic acid receptor (RAR) and the like (see Mangelsdorf et al (1995) *Cell* 83, 835–839 for a review and nomenclature).

It is particularly preferred if the steroid hormone receptor protein is estrogen receptor (ER).

As noted, DNA binding proteins may be engineered so as to bind to a particular, selected target DNA sequence which is at or associated with a selected gene. In one embodiment of the invention the DNA binding protein is one which has been engineered to bind to a site which is present in a mutant gene sequence within the plant or animal cell but is not present in the equivalent wild type sequence. For example, and as is discussed in more detail below, the engineered DNA binding portion may bind selectively to a dominant negative, mutated gene, such as a mutant oncogene and, upon binding, chromatin inactivation occurs and suppresses the expression of the mutant oncogene. Examples of oncogenes mutated in human cancer include RAS (H-ras) and Bcl-10.

Typically, the DNA binding portion and the chromatin inactivation portion are fused such that the fusion polypeptide may be encoded by a nucleic acid molecule. Suitably, the DNA binding portion and the chromatin inactivation portion are joined so that both portions retain their respective activities such that the polypeptide may bind to a site present in a plant or animal genome and, upon binding, the chromatin inactivation portion is still able to inactivate chromatin. The two portions may be joined directly, but they may be joined by a linker peptide. Suitable linker peptides are those that typically adopt a random coil conformation, for example the polypeptide may contain alanine or proline or a mixture of alanine plus proline residues. Preferably, the linker contains between 10 and 100 amino acid residues, more preferably between 10 and 50 and still more preferably between 10 and 20. In any event, whether or not there is a linker between the portions of the polypeptide the polypeptide is able to bind its target DNA and is able to inactivate chromatin thereby selectively suppressing or inactivating gene expression.

A further aspect of the invention provides a polynucleotide encoding a polypeptide of the invention. In particular, the invention provides a polynucleotide wherein the nucleic acid binding portion and the chromatin inactivation portion are fused such that the fusion polypeptide is encoded by a single open reading frame of the polynucleotide. The polynucleotide may be DNA or RNA; DNA is preferred. DNA may or may not contain introns but, in any case, the polynucleotide encodes a polypeptide of the invention.

Polynucleotides which encode suitable nucleic acid binding portions, particularly DNA binding portions are known in the art or can be readily designed from known sequences such as from known sequences contained in scientific publications or contained in nucleotide sequence databases such as the GenBank, EMBL and dbEST databases. Polynucleotides which encode suitable chromatin inactivation portions are known in the art or can readily be designed from known sequences and made. Polynucleotide sequences encoding various suitable chromatin inactivation portions are given above in the references which refer to the polypeptides or are available from GenBank or EMBL or dbEST. A reference for PLZF is Chen et al (1993) *EMBO J.* 12, 1161–1167.

Polynucleotides which encode suitable linker peptides can readily be designed from linker peptide sequences and made.

Thus, polynucleotides which encode the polypeptides of the invention can readily be constructed using well known genetic engineering techniques.

A variety of methods have been developed to operably link polynucleotides, especially DNA, to other polynucleotides, including vectors, for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. Coli* DNA polymerase I, enzymes that remove protruding, 3'-single-stranded termini with their 3'–5'-exonucleolytic activities, and fill in recessed 3'-ends with their polymerising activities.

The combination of these activities therefore generates blunt-ended DNA segments. The blunt-ended segments are then incubated with a large molar excess of linker molecules in the presence of an enzyme that is able to catalyse the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487–491. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

Methods of joining a polynucleotide to a nucleic acid vector are, of course, applicable to joining any polynucleotides.

The DNA (or in the case of retroviral vectors, RNA) is then expressed in a suitable host to produce a polypeptide of the invention. Thus, the DNA encoding the polypeptide of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA (or in the case of retroviral vectors, RNA) encoding the polypeptide of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention. It is preferred that the promoter is one which can be regulated. It is particularly preferred if the promoter is an inducible promoter which can be selectively induced at an appropriate time once the vector has been introduced into the eukaryotic cell. It will be appreciated that upon induction, the polypeptide of the invention may be expressed in the cell and exert its effect. In this situation, induction of expression of the polypeptide of the invention leads to suppression of the targeted gene. Inducible promoters are known in the art for many eukaryotic cells including plant and animal cells. These include heat-shock-, glucocorticoid-, oestradiol-, and metal-inducible promoter systems.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps).

Plant transformation vectors are well known in the art. For example, vectors for *Agrobacterium*-mediated transformation are available from the Centre for the Application of Molecular Biology to International Agriculture, GPO Box 3200, Canberra, ACT 2601, Australia (cambia@cambia.org.au).

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include plant, yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Protoplasts for transformation are typically generated as required by methods known in the art. Plant cell lines are not generally available. However, one cell line which is commonly used is the Bright Yellow 2 cell line from tobacco (BY2; Mu et al (1997) *Plant Mol. Biol.* 34, 357–362).

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. With regard to plant cells and whole plants three plant transformation approaches are typically used (J. Draper and R. Scott in D. Grierson (ed.), "Plant Genetic Engineering", Blackie, Glasgow and London, 1991, vol. 1, pp 38–81):

i) *Agrobacterium*-mediated transformation, using the Ti plasmid of *A. tumefaciens* and the Ri plasmid of *A. rhizogenes* (P. Armitage, R. Walden and J. Draper in J. Draper, R. Scott, P. Armitage and R. Walden (eds.), "Plant Genetic Transformation and Expression—A Laboratory Manual", Blackwell Scientific Publications, Oxford, 1988, pp 1–67; R. J. Draper, R. Scott and J. Hamill ibid., pp 69–160);

*Agrobacterium*-mediated transformation is also described in Hooykaas & Schilperoot (1992) *Plant Mol. Biol.* 19, 15–38; Zupan & Zambryski (1995) *Plant Physiol.* 107, 1041–1047; and Baron & Zambryski (1996) *Curr. Biol.* 6, 1567–1569.

ii) DNA-mediated gene transfer, by polyethylene glycol-stimulated DNA uptake into protoplasts, by electroporation, or by microinjection of protoplasts or plant cells (J. Draper, R. Scott, A. Kumar and G. Dury, ibid., pp 161–198). Direct gene transfer into protoplasts is also described in Neuhaus & Spangenberg (1990) *Physiol. Plant* 79, 213–217; Gad et al (1990) *Physiol. Plant* 79, 177–183; and Mathur & Koncz (1998) *Method Mol. Biol.* 82, 267–276;

iii) transformation using particle bombardment (D. McCabe and P. Christou, *Plant Cell Tiss. Org. Cult.*, 3, 227–236 (1993); P. Christou, *Plant J.*, 3, 275–281 (1992)).

Some species are amenable to direct transformation, avoiding a requirement for tissue or cell culture (Bechtold et al (1993) *Life Sciences*, C.R. Acad. Sci. Paris 316, 1194–1199).

*Agrobacterium*-mediated transformation is generally less effective for monocotyledonous plants for which approaches ii) and iii) are therefore preferred. However, *Agrobacterium* is capable of transferring DNA to some monocotyledenous plants if tissues containing "competent" cells are infected (see Hiei et al (1997) *Plant Mol. Biol.* 35, 205–218). In all approaches a suitable selection marker, such as kanamycin- or herbicide-resistance, is preferred or alternatively a screenable marker ("reporter") gene, such as β-glucuronidase or luciferase (see J. Draper and R. Scott in D. Grierson (ed.), "Plant Genetic Engineering", Blackie, Glasgow and London, 1991, vol. 1 pp 38–81).

Electroporation is also useful for transforming and/or transfecting cells and is well known in the art for transforming yeast cell, bacterial cells, insect cells, vertebrate cells and some plant cells (eg barley cells, see Lazzeri (1995) *Methods Mol. Biol.* 49, 95–106).

For example, many bacterial species may be transformed by the methods described in Luchansky et al (1988) *Mol. Microbiol.* 2, 637–646 incorporated herein by reference. The greatest number of transformants is consistently recovered following electroporation of the DNA-cell mixture suspended in 2.5× PEB using 6250V per cm at 25 µFD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the polypeptide. For example, cells successfully transformed with an expression vector produce polypeptides displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

In relation to plants, it is envisaged that the invention includes single cell derived cell suspension cultures, isolated protoplasts or stable transformed plants. In the latter case it is preferred if the polypeptide of the invention is expressed using an inducible promoter system to avoid potentially lethal effects of gene down-regulation during regeneration of homozygous plants.

Although the polypeptides or polynucleotides of the invention may be introduced into any suitable host cell, it will be appreciated that they are primarily designed to be effective in appropriate animal or plant cells, particularly those that have one or more sites within their DNA to which the polypeptide of the invention may bind.

Thus, the animal of plant cells which contain a polypeptide (or polynucleotide) of the invention whose presence suppresses the expression of a particular gene, or the animals or plants containing these cells, may be considered to have the gene "knocked out" in the sense that it can no longer be expressed. The chromatin inactivation by histone deacetylation may be irreversible.

It will be readily appreciated that introduction of a polypeptide of the invention into an animal or plant cell, or introduction and expression of a polynucleotide encoding a polypeptide of the invention in an animal or plant cell, will allow targeting of the polypeptide to an appropriate binding site within the DNA (and which is bound by the DNA-binding portion of the polypeptide) and allow for the chromatin at or associated with the target binding site to be inactivated so as to lead to suppression or inactivation of gene expression. Typically, the polypeptide of the invention is selected so that it targets a selected gene. Thus, suitably, the targeted gene has a site which is bound by the DNA binding portion of the polypeptide associated with it. The site which is so bound may be within the gene itself, for example within an intron or within an exon of the gene; or it may be in a region 5' of the transcribed portion of the gene, for example within or adjacent to a promoter or enhancer region; or it may be in a region 3' of the transcribed portion of the gene.

Genes regulated by oestrogen receptor (ER) include the progesterone receptor (PR) gene and the PS2 (trefoil related protein) gene. Thus, the method of the invention may be used to inactivate the PR gene or the PS2 gene when the DNA binding portion of the compound of the invention is at least the DNA-binding portion of ER. Anti-oestrogen therapy is used in the treatment of breast cancer. The full repertoire of oestrogen regulated genes involved in breast cancer is presently unknown. It is generally considered that anti-oestrogen therapy results in the altered expression of key oestrogen regulated genes involved in breast cancer cell growth and transformation. The methods of the invention described below may provide an alternative, potentially more effective, way of regulating the expression (particularly inhibiting) of oestrogen-responsive genes. It may be that for certain DNA binding portions, in a given plant or animal cell there is only one target site and the expression of only one gene is suppressed by the chromatin inactivation portion. However, there may be more than one target site and introduction of a polypeptide (or polynucleotide) of the invention may lead to suppression of expression of a number of genes.

Thus, a further aspect of the invention provides a method of suppressing the expression of a selected gene in a eukaryotic cell the method comprising introducing into the cell (a) a polypeptide comprising a nucleic acid binding portion which binds to a site at or associated with the selected gene which site is present in a eukaryotic genome and a chromatin inactivation portion, or (b) a polynucleotide encoding said polypeptide.

Suitably, the polypeptide is a polypeptide of the invention as described above. Also suitably, the polynucleotide is a polynucleotide of the invention as described above. It is preferred if the preferred polypeptides or polynucleotides of the invention are used in the method. In particular, it is preferred that the chromatin inactivation portion is PLZF or a portion thereof, for example a portion that can facilitate histone deacetylation. Although it may be a site which has been engineered into the cell, it is preferred if the site at or associated with the selected gene is naturally present in the eukaryotic genome. Preferably, the eukaryotic cell is a plant cell or an animal cell.

The ability to suppress the expression of a selected gene is useful in many areas of biology.

Typically, when the gene whose expression is suppressed is in an animal cell, the animal cell is a cell within an animal and the method of the invention is used to suppress the expression of a selected gene in an animal. For the avoidance of doubt, animal in this context includes human. Examples of particular uses in animal cells include allele-specific inactivation of oncogenic proteins such as mutant Ras and mutant Bcl-10; inhibition of oestrogen receptor regulated gene expression in breast cancer; inhibition of androgen receptor; inhibition of genes of interest for developmental studies; inhibition of genes for developing transgenic models of human diseases; and inhibition of genes involved in tissue modelling, as found in cancer and wound healing.

Also typically, the plant cell is a cell within a plant and the method of the invention is used to suppress the expression of a selected gene in a plant.

In one embodiment, the method of the invention is used to suppress the expression of socially or environmentally unacceptable or undesirable genes in commercially engineered transgenic plants. Such genes may include, for example, antibiotic or herbicide selectable marker genes. In this embodiment, the gene in the transgenic plant is targeted for silencing.

In a further embodiment of the invention novel plant architecture or floral morphology may be achieved by targeting some known homeotic genes involved in these developmental pathways.

Suitably, the method of the invention is used to suppress or inactivate the expression of a gene whose expression it is desirable to suppress or inactivate. Such genes include oncogenes, viral genes including genes present in proviral genomes and so the method in relation to animals may constitute a method of medical treatment. Oncogenes may be overexpressed in certain cancers and it may be desirable to suppress their expression. Some oncogenes are oncogenic by virtue of having an activating mutation. Using the method of the invention the selective suppression of expression of a mutant oncogene may be achieved using a DNA binding portion that selectively binds to the mutant oncogene sequence and wherein the chromatin inactivation portion inactivates the chromatin in which the oncogene resides or with which it is associated so that expression of the mutant oncogene is suppressed. Suppression of oncogene overexpression or of mutant (especially activated) oncogene expression is generally desirable in treating cancers in which the oncogenes play a role. Mutant oncogenes which may be targeted by the method of the invention include Ras and Bcl-10. These may be targeted by engineered DNA binding proteins capable of recognising the mutated genes in a sequence specific manner.

The expression of viral genes in an animal or plant cell is generally undesirable since this expression is often associated with pathogenesis. The nucleic acid of certain viruses may be formed into chromatin and the expression of such viral genes may be controlled by modification of this chromatin. For example, retroviral proviruses (ie DNA copies of retroviral RNAs) are often incorporated into animal and plant genomes where they become part of the chromatin, for example, integrated HIV provirus and integrated human papillomavirus. Gypsy and Copia-like retrotransposons appear to be widely distributed in the plant kingdom. Copia-like retrotransposons, or at least their reverse transcriptase domains, appear broadly distributed in higher plants while the Gypsy-like elements (which share their organisation with the retroviruses but lack retroviral envelope domains) are less abundant (Suoniemi et al (1998) *Plant J.* 13, 699–705). Integration of viral DNA into the plant genome has been demonstrated for geminiviral DNA into the tobacco nuclear genome (Bejarano et al (1996) *Proc. Natl. Acad. Sci. USA* 93, 759–764). Potential retroviruses have also recently been described in plants (Wright & Voytus (1998) *Genetics* 149, 703–715). Using the method of the invention the selective suppression of expression of a viral gene may be achieved. Engineered DNA binding proteins, or RNA binding proteins, such as HIV tat protein, may be used to target a chromatin inactivation portion and lead to proviral genome inactivation by binding to nascent genomic RNA transcripts, achieving histone deacetylation by proximity.

Certain genetic diseases are caused by dominant mutations, such as achondroplasia. Suppression of expression of the mutant allele may be useful in treating these diseases. Using the method of the invention the selective suppression of expression of the mutant allele may be achieved using a DNA binding portion that selectively binds to the mutant allele sequence and wherein the chromatin inactivation portion inactivates the chromatin in which the mutant allele resides or with which it is associated so that expression of the mutant allele is suppressed.

These methods of the invention typically and preferably involve the transfer of a polynucleotide encoding said polypeptide into an animal or plant cell.

Gene transfer systems known in the art may be useful in the practice of the methods of the present invention in which the polynucleotide of the invention is introduced into a cell either within or out with an animal body. Such an introduction of a polynucleotide may be therapeutically useful and constitutes a form of gene therapy. These include viral and nonviral transfer methods. A number of viruses have been used as gene transfer vectors, including papovaviruses, eg SV40 (Madzak et al (1992) *J. Gen. Virol.* 73, 1533–1536), adenovirus (Berkner (1992) *Curr. Top. Microbiol. Immunol.* 158, 39–61; Berkner et al (1988) *BioTechniques* 6, 616–629; Gorziglia and Kapikian (1992) *J. Virol.* 66, 4407–4412; Quantin et al (1992) *Proc. Natl. Acad. Sci. USA* 89, 2581–2584; Rosenfeld et al (1992) *Cell* 68, 143–155; Wilkinson et al (1992) *Nucleic Acids Res.* 20, 2233–2239; Stratford-Perricaudet et al (1990) *Hum. Gene Ther.* 1, 241–256), vaccinia virus (Moss (1992) *Curr. Top. Microbiol. Immunol.* 158, 25–38), adeno-associated virus (Muzyczka (1992) *Curr. Top. Microbiol. Immunol.* 158, 97–123; Ohi et al (1990) *Gene* 89, 279–282), herpes viruses including HSV and EBV (Margolskee (1992) *Curr. Top. Microbiol. Immunol.* 158, 67–90; Johnson et al (1992) *J. Virol.* 66, 2952–2965; Fink et al (1992) *Hum. Gene Ther.* 3, 11–19; Breakfield and Geller (1987) *Mol. Neurobiol.* 1, 337–371; Freese et al (1990) *Biochem. Pharmacol.* 40, 2189–2199), and retroviruses of avian (Brandyopadhyay and Temin (1984) *Mol. Cell. Biol.* 4, 749–754; Petropoulos et al (1992) *J. Virol.* 66, 3391–3397), murine (Miller (1992) *Curr. Top. Microbiol. Immunol.* 158, 1–24; Miller et al (1985) *Mol. Cell. Biol.* 5, 431–437; Sorge et al (1984) *Mol. Cell. Biol.* 4, 1730–1737; Mann and Baltimore (1985) *J. Virol.* 54, 401–407; Miller et al (1988) *J. Virol.* 62, 4337–4345), and human origin (Shimada et al (1991) *J. Clin. Invest.* 88, 1043–1047; Helseth et al (1990) *J. Virol.* 64, 2416–2420; Page et al (1990) *J. Virol.* 64, 5370–5276; Buchschacher and Panganiban (1992) *J. Virol.* 66, 2731–2739). To date most human gene therapy protocols have been based on disabled murine retroviruses.

Nonviral gene transfer methods known in the art include chemical techniques such as calcium phosphate coprecipitation (Graham and van der Eb (1973) *Virology* 52, 456–467; Pellicer et al (1980) *Science* 209, 1414–1422); mechanical techniques, for example microinjection (Anderson et al (1980) *Proc. Natl. Acad. Sci. USA* 77, 5399–5403; Gordon et al, 1980; Brinster et al (1981) *Cell* 27, 223–231; Constantini and Lacy (1981) *Nature* 294, 92–94); membrane fusion-mediated transfer via liposomes (Felgner et al (1987) *Proc. Natl. Acad. Sci. USA* 84, 7413–7417; Wang and Huang (1989) *Biochemistry* 28, 9508–9514; Kaneda et al (1989) *J. Biol. Chem.* 264, 12126–12129; Stewart et al (1992) *Hum. Gene Ther.* 3, 267–275; Nabel et al, 1990; Lim et al (1992) *Circulation* 83, 2007–2011); and direct DNA uptake and receptor-mediated DNA transfer (Wolff et al (1990) *Science* 247, 1465–1468; Wu et al (1991) *J. Biol. Chem.* 266, 14338–14342; Zenke et al (1990) *Proc. Natl. Acad. Sci. USA* 87, 3655–3659; Wu et al, 1989b; Wolff et al (1991) *BioTechniques* 11, 474–485; Wagner et al, 1990; Wagner et al (1991) *Proc. Natl. Acad. Sci. USA* 88, 4255–4259; Cotten et al (1990) *Proc. Natl. Acad. Sci. USA* 87, 4033–4037; Curiel et al (1991a) *Proc. Natl. Acad. Sci. USA* 88, 8850–8854; Curiel et al (1991b) *Hum. Gene Ther.* 3, 147–154). Viral-mediated gene transfer can be combined with direct in vivo gene transfer using liposome delivery, allowing one to direct the viral vectors to the tumour cells and not into the surrounding nondividing cells. Alternatively, the retroviral vector producer cell line can be injected into tumours (Culver et al (1992) *Science* 256, 1550–1552). Injection of producer cells would then provide a continuous source of vector particles. This technique has been approved for use in humans with inoperable brain tumours.

Other suitable systems include the retroviral-adenoviral hybrid system described by Feng et al (1997) *Nature Biotechnology* 15, 866–870, or viral systems with targeting ligands such as suitable single chain Fv fragments.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumour deposits, for example, following direct in situ administration (Nabel (1992) *Hum. Gene Ther.* 3, 399–410). Gene transfer techniques which target DNA directly to a target cell or tissue, is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

It may be advantageous if the polypeptide of the invention is expressed in the target cell using an inducible promoter. Examples of suitable inducible promoters include those that can be induced by heat shock, glucocorticoids, oestradiol and metal ions.

Preferably, the method of suppressing the expression of a selected gene is used to suppress expression of a gene in a human cell; in one particularly preferred embodiment the human cell is within a human body.

However, the method of the invention may involve the modification of animal cells (including human cells) outside of the body of an animal (ie an ex vivo treatment of the cells) and the so modified cells may be reintroduced into the animal body.

From the foregoing, it will be appreciated that the method of the invention may be useful to suppress the activity of a plurality of selected genes. In particular, the method of the invention may be used to suppress the activity of a group of genes whose expression is controlled, at least to a large extent, by a single transcription factor. For example, the method may be used to suppress oestrogen-regulated genes as is described in more detail in the Examples.

A further aspect of the invention provides use of a polypeptide comprising a nucleic acid binding portion which binds to a site at or associated with a selected gene which site is naturally present in a eukaryotic genome and a chromatin inactivation portion in the manufacture of an agent for suppressing the expression of the selected gene in a eukaryotic cell.

A still further aspect of the invention provides use of a polynucleotide encoding a polypeptide comprising a nucleic acid binding portion which binds to a site at or associated with a selected gene which site is naturally present in a eukaryotic genome and a chromatin inactivation portion in the manufacture of an agent for suppressing the expression of the selected gene in a eukaryotic cell.

It will be appreciated that it is particularly preferred if the polypeptide or polynucleotide is used in the preparation of a medicament for suppressing the expression of a selected gene in an animal. For the avoidance of doubt, by "animal" we include human.

A further aspect of the invention provides a method of treating a patient in need of suppression of the expression of a selected gene, the method comprising administering to the patient an effective amount of a polypeptide comprising a nucleic acid binding portion which binds to a site at or associated with the selected gene and a chromatin inactivation portion.

A still further aspect of the invention provides a method of treating a patient in need of suppression of the expression of a selected gene, the method comprising administering to the patient an effective amount of a polynucleotide encoding a polypeptide comprising a nucleic acid binding portion which binds to a site at or associated with the selected gene and a chromatin inactivation portion.

It will be appreciated that suppression of the expression of a selected gene is useful where the expression or overexpression of the selected gene is undesirable and contributes to a disease state in the patient. Examples of undesirable expression of a gene include the expression of certain activated oncogenes in cancer.

Suppression of the expression of the ER upregulated genes is desirable in the treatment of breast cancer. Similarly, suppression of the expression of the androgen receptor (AR)-regulated genes is desirable in the treatment of prostate cancer.

Further aspects of the invention provides use of a polypeptide comprising a nucleic acid binding portion which binds to a site at or associated with a selected gene and a chromatin inactivation portion in the manufacture of a medicament for suppressing the expression of a selected gene in a patient in need of such suppression; and the use of a polynucleotide encoding a polypeptide comprising a nucleic acid binding portion which binds to a site at or associated with a selected gene and a chromatin inactivation portion in the manufacture of a medicament for suppressing the expression of a selected gene in a patient in need of such suppression.

Still further aspects of the invention provides a polypeptide comprising a nucleic acid binding portion which binds to a site at or associated with a selected gene and a chromatin inactivation portion for use in medicine; and a polynucleotide encoding a polypeptide comprising a nucleic acid binding portion which binds to a site at or associated with a selected gene and a chromatin inactivation portion for use in medicine. Thus, the polypeptide or polynucleotide are packaged and presented for use in medicine.

Yet still further aspects of the invention provide a pharmaceutical composition polypeptide comprising a nucleic acid binding portion which binds to a site at or associated with a selected gene and a chromatin inactivation portion and a pharmaceutically acceptable carrier; and a pharmaceutical composition comprising a polynucleotide encoding a polypeptide comprising a nucleic acid binding portion which binds to a site at or associated with a selected gene and a chromatin inactivation portion and a pharmaceutically acceptable carrier.

By "pharmaceutically acceptable" is included that the formulation is sterile and pyrogen free. Suitable pharmaceutical carriers are well known in the art of pharmacy.

The invention will now be described in more detail with reference to the following Figures and Examples wherein:

FIG. 1 shows a schematic representation of the HDAC complex. The schematic representation shows components of the HDAC complex, which includes the Nuclear Receptor Interacting Proteins N-Cor (and SMRT), Sin3, SAP18, SAP30 and RbAp48. It is currently believed that the complex contains HDAC1 and 2 (shown here simply as HDAC). The Nuclear Receptors shown here (Retinoid X Receptor (RXR and its partners Retinoic Acid Receptor α (RAR) or Thyroid Hormone Receptor (TR)) serve as examples of Nuclear Receptors. DNA is represented by the coil and histones as spheres. The arrows emanating from HDAC indicate that HDAC deacetylates histones. The arrow originating from the DNA represents a transcription start site. The postulated effect of histone deacetylation is inhibition of transcription.

Figure 2:
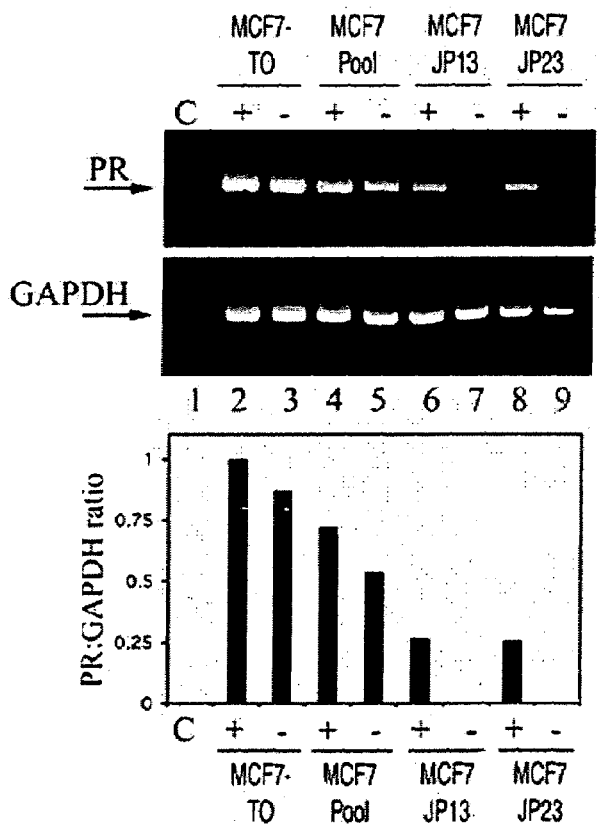
FIG. 2 is a schematic representation of the receptors and PLZF.

FIG. 2. Schematic representation of the receptors and PLZF. The domain structure of retinoic acid receptor α (RARα) and oestrogen receptor α (ERα) are shown. Regions A–F refer to regions of differing amino-acid sequence homology as first described by Krust et al (1986) EMBO J. 5, 891–897, the DNA binding domain (DBD, region C) and the ligand binding domain (LBD, region E) are most well conserved between the receptors. Transcription Activation Functions 1 and 2 (AF-1 and AF-2) refer to the regions of the receptor containing sequences required for transcriptional activation. The LBD also contains sequences which interact with co-repressor proteins. PLZF-RARα shows the fusion protein in acute promyelocytic leukaemia which results from the t(11;17) translocation, fusing the first 455 amino-acids of PLZF with regions B–F of RARα (described by Chen et al (1993) EMBO J. 12, 1161–1167). The PLZF-ER construct which we have made is shown, fusing the first 455 amino-acids of PLZF with ERα sequences (amino-acids 151–595) homologous to the RARα sequences present in PLZF-RARα. Also shown is HEG19 (see Tora et al (1989) EMBO J. 8, 1981–1986 which contains amino-acids 180–595 of human ERα. The open circles with the lettering $Zn^{++}$ show the positions of the Kruppel-like $Zinc^{++}$-binding fingers present in PLZF.

FIG. 3. Comparison of the in vitro DNA binding by wild-type human ERα and PLZF-ER. (A, B) COS-1 cells were transiently transfected with 5 μg of pSG5 (lane 1), human ERα (HEG0, lane 2), HEG19 (lane 3), PLZF-ERα (lane 4) or PLZF (lane 5). (A) Lysates were prepared in HS buffer and gel shifts performed using [$^{32}$P]-labelled ERE, followed by fractionation on a 5% non-denaturing polyacrylamide gel and visualised by autoradiography. The uncomplexed ERE is seen at the bottom of the gel whilst receptor-complexed ERE migrates more slowly. (B) Lysates prepared for (A) were run on a 10% SDS-polyacrylamide gel, proteins were transferred to nitrocellulose and immunoblotting performed using a monoclonal antibody F3, raised against the C-terminal portion of human ERα. The band at 68 kDal seen in each lane is a cross-reacting protein unrelated to the oestrogen receptor (Ali et al (1993) Hybridoma 12, 391–405). Molecular mass marker sizes are listed on the right in kDal.

Figure 4A:
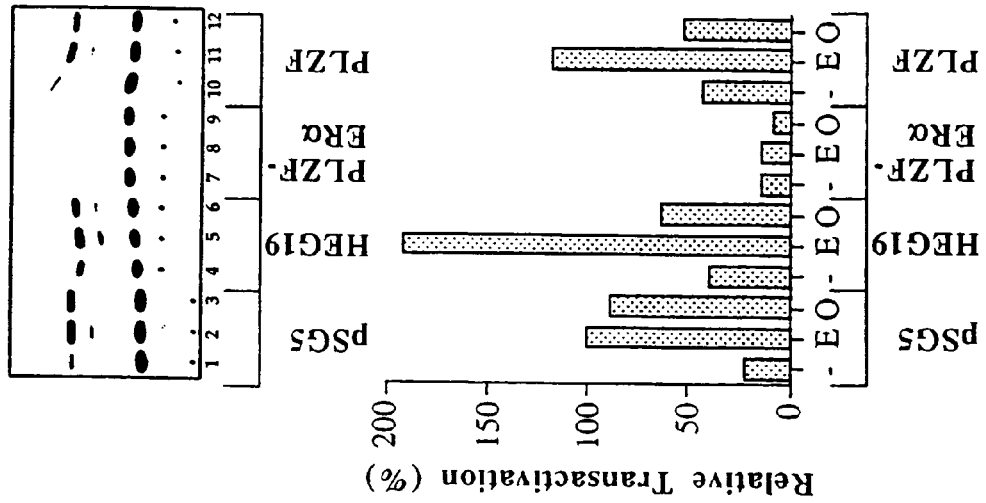
FIG. 4A illustrates that PLZF-ERα does not activate an oestrogen-responsive reporter gene and the presence or absence of oestrogen.

FIG. 4A. PLZF-ERα does not activate an oestrogen-responsive reporter gene in the presence or absence of oestrogen. The oestrogen receptor-negative mammalian COS-1 cell line was transiently co-transfected with 2 μg of the reporter gene 17M-ERE-G-CAT and 1 μg of the β-galactosidase reporter gene pCH110 (from Pharmacia, UK), together with 0.5 μg of the expression plasmid pSG5 (lanes 1–3), HEG0 (lanes 4–6), HEG19 (lanes 7–9), PLZF-ERα (lanes 10–12) or PLZF (lanes 13–15), as indicated, together with the plasmid BSM to a total DNA concentration of 20 μg. 17β-oestradiol (E, 10 nM) or 4-hydroxy-tamoxifen (O, 100 nM) or prepared in ethanol were added where appropriate. Ethanol was added in the no ligand control. CAT activities were assayed after normalization for β-galactosidase activity from the reference plasmid pCH110. The top panel shows the autoradiographic image. The lower panel shows the result of quantification of four representative experiments. The transcriptional activities are depicted as percentage of the activity observed with HEG0 in the presence of 17β-oestradiol (taken as 100%). For these studies 17β-oestradiol, 4-hydroxytamoxifen and acetyl CoA were purchased from Sigma, UK. $^{14}$C-labelled chloramphenicol was purchased from Amersham International, UK. The other reagents are commonly available from a variety of commercial sources. For more details on the procedures see Metzger et al (1995) Mol. Endocrinol. 9, 579–591.

Figure 4B:
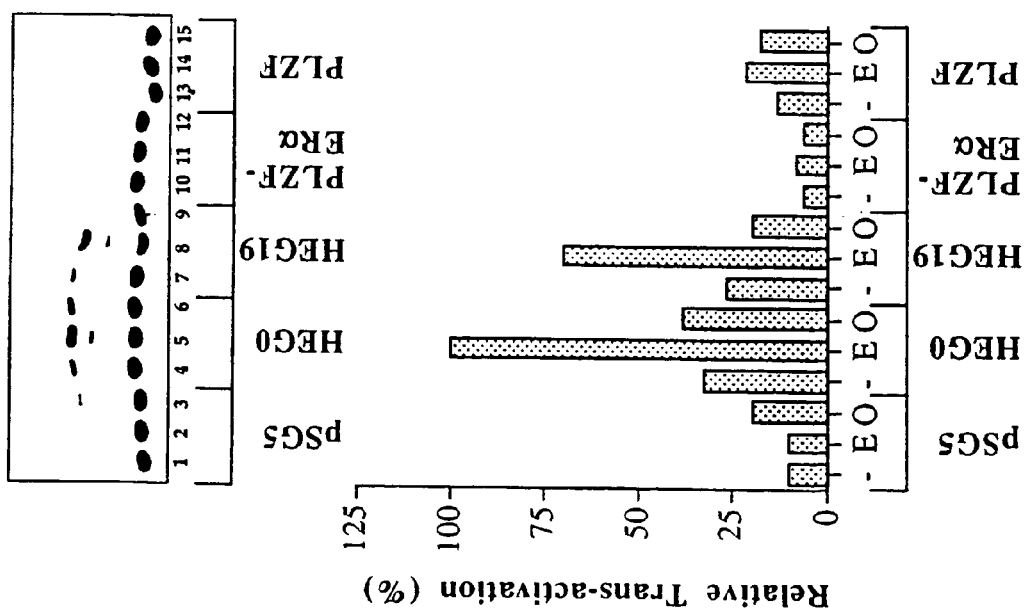
FIG. 4B illustrates that PLZF-ERα represses activation of an oestrgen-responsive reporter gene.

FIG. 4B. PLZF-ERA represses activation of an oestrogen-responsive reporter gene. The ER-positive breast cancer cell line, MCF-7 was transiently co-transfected with 2 μg of the reporter gene 17M-ERE-G-CAT and 5 μg of the β-galactosidase reporter gene pCH110, together with 0.5 μg of the expression plasmid (pSG5 (lanes 1–3), HEG19 (lanes 4–6), PLZF-ERα (lanes 7–9) or PLZF (lanes 10–12), as indicated, together with the plasmid BSM to a total DNA concentration of 20 μg. Ligands were added and samples processed as described for FIG. 4A. The transcriptional activities are depicted as percentage of the activity observed with pSG5 in the presence of 17β-oestradiol (lane 2; taken as 100%).

FIG. 5 shows the alignment of the amino-acid sequence encoding HDAC1 from man, arabidopsis and yeast. The aligned amino-acid sequences are shown using the one letter code. The sequences in the figure further correspond to SEQ ID No:6 (human HDAC polypeptide); SEQ ID NO:7 (*arabidopsis thaliana* HDAC polypeptide); and SEQ ID NO:8 (yeast HDAC polypeptide) in the Sequence Listing. The asterisks mark the positions of amino-acids which are identical in all three sequences, whilst the dots show positions of amino-acids which are conservative changes. This alignment is simply meant to illustrate that HDAC genes are present in all eukaryotes from yeast and plants to man and is not an exhaustive list of all known sequences. Note further that a total of six mammalian HDAC genes have been described (see Grozinger et al (1999) *Proc. Natl. Acad. Sci. USA* 96, 4868–4873).

Figure 6:
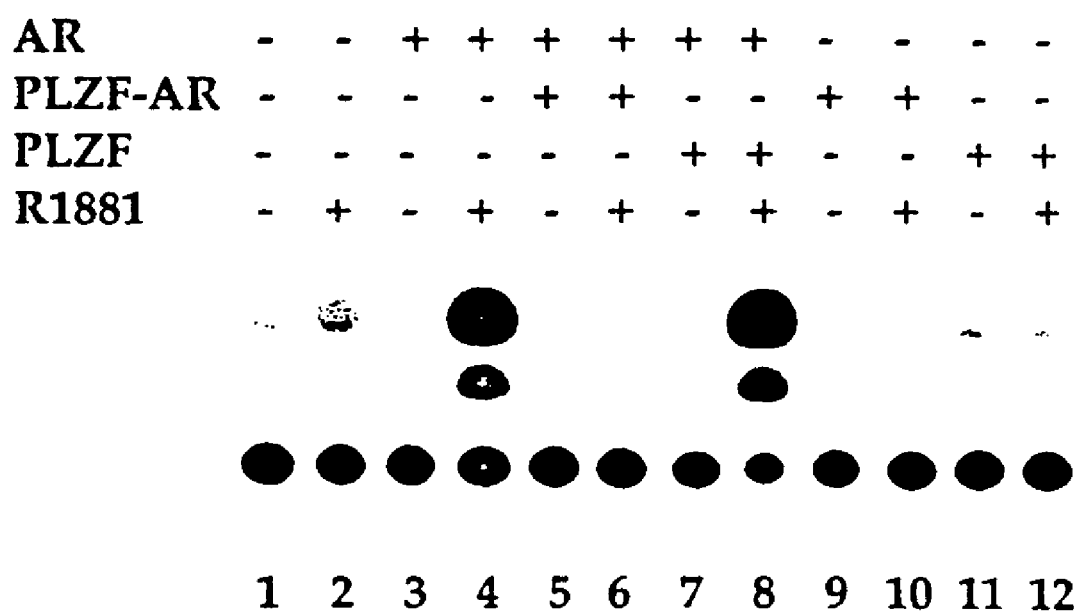
FIG. 6 shows that PLZF-AR represses activation of an androgen-responsive reporter gene.

FIG. 6 shows that PLZF-AR represses activation of an androgen-responsive reporter gene. COS-1 cells were co-transfected with 2 µg of the reporter gene pG29G-tk-CAT and 1 µg of the β-galactosidase reporter plasmid pSGΔlacZ together with 2 µg of the expression plasmid pSG5 (lanes 1–2), or 1 µg of pSG5 (lanes 34, 9–12), AR (lanes 3–8), PLZF-AR (lanes 5–6, 9–10) or PLZF (lanes 7–8, 11–12), as indicated, in the presence or absence of R1881 (1 nM), prepared in ethanol. R1881 is a potent activator of the androgen receptor, for example see Quarmby et al (1990) *Mol. Endocrinol.* 4, 1399–4107. Ethanol was added to the control samples (-).

EXAMPLE 1

Construction and Use of PLZF-ERα Gene Fusion

Work was carried out to produce an analogue of the PLZF-RARα gene fusion found in acute promyelocytic leukaemia (Guidez et al (1998) *Blood* 91, 2634–2642), in which the RARα portion was replaced by an equivalent region of the human estrogen receptor (ERα). To do this, a 1392 bp region of PLZF coding region was amplified by PCR from a full length cDNA clone using a generic oligonucleotide primer to 5' flanking cloning vector sequence (T7 primer) and a primer complementary to PLZF sequences encompassed by bases 1441–1446 of the sequence of Chen et al (1993) *EMBO J.* 12, 1161–1167, with additional bases added to the 3' end, so as to introduce an in-frame XhoI restriction enzyme site (Primer PLZF R; ccgctcgagCT-GAATGAGCCAGTAAGTGCATTCTC) (SEQ ID NO:1). Similarly, a 1407 bp region of a human ER RARα cDNA clone (HEG0; Tora et al (1989) *EMBO J.* 8, 1981–1986) was amplified by PCR using primers which introduced an in frame XhoI site into 5' coding region and a BamHI site into the 3' untranslated region (Primers ER F1; CCGCTC-GAGggccaaattcagataatcgac (SEQ ID NO:2) and ER R1; ccgtgtgggaTccagggagctctca (SEQ ID NO:3)). PLZF and ER PCR products were restriction enzyme digested with EcoRI and XhoI and XhoI and BamHI respectively. The digest products were purified and ligated with pSG5 expression vector DNA (Stratagene) previously digested with the restriction enzymes EcoR1 and BamHI. The ligation product was used to transform *E. coli* bacteria and plasmid DNA prepared from individual clones. Recombinant pSG5 plasmids containing PLZF-ER gene fusion DNA were initially identified by restriction enzyme digestion and were subsequently confirmed by DNA sequence analysis. The resultant cloned PLZF-ER gene encodes the first 455 amino acids of PLZF, fused in frame with amino acids 151–595 of human ERα sequence. This clone was used in experiments to address expression and subsequent inhibition of ER regulated gene activity by the PLZF-ER fusion protein, as shown in FIGS. 3 and 4.

FIG. 3 shows a comparison of the in vitro DNA binding by wild-type human ERα and PLZF-ERα. (A, B) COS-1 cells were transiently transfected with 5 µg of pSG5 (lane 1), human ERα (HEG0, lane 2), HEG19 (lane 3), PLZF-ERα (lane 4) or PLZF (lane 5). (A) Lysates were prepared in HS buffer and gel shifts performed using [$^{32}$P]-labelled ERE, followed by fractionation on a 5% non-denaturing polyacrylamide gel and visualised by autoradiography. The uncomplexed ERE is seen at the bottom of the gel whilst receptor-complexed ERE migrates more slowly. (B) Lysates prepared for (A) were run on a 10% SDS-polyacrylamide gel, proteins were transferred to nitrocellulose and immunoblotting performed using a monoclonal antibody F3, raised against the C-terminal portion of human ERα. The band at 68 kDal seen in each lane is a cross-reacting protein unrelated to the oestrogen receptor. Molecular mass marker sizes are listed on the right in kDal.

The ability of PLZF-ERα to activate transcription of oestrogen responsive genes was tested in the oestrogen receptor-negative COS-1 cells. COS-1 cells were transiently transfected with an oestrogen responsive reporter gene 17M-ERE-G-CAT. Activation of gene expression results in synthesis of the bacterial chloramphenicol acetyl transferase (CAT) protein whose enzymatic activity can be assayed in vitro using $^{14}$C-labelled chloramphenicol and acetyl CoA. Acetylation of $^{14}$C-chloramphenicol can be visualised using thin layer chromatography and autoradiography. Quantitation is performed using phosphorimager analysis (Bio-Rad, UK) (see Metzger et al (1995) *Mol. Endocrinol.* 9, 579–591 for details of procedures). Normalization for variations in transfection efficiency is carried out by co-transfection of the reporter gene with a β-galactosidase expression plasmid (pCH110). As well as the two reporter genes the cells were transfected with the expression vector pSG5 (lanes 1–3), HEG0 (lanes 4–6), HEG19 (lanes 7–9), PLZF-ERα (lanes 10–12) or PLZF (lanes 13–15). Ligands (17β-oestradiol (10 nM, lanes 2, 5, 8, 11, 14) or 4-hydroxytamoxifen (100 nM, lanes 3, 6, 9, 12, 15) were added. The ligands were prepared in ethanol so an equal volume of ethanol was added to the no ligand controls (lanes 1, 4, 7, 10, 13). The results show that the CAT reporter gene activity is increased in the presence of E2 when HEG0 or HEG19 are expressed (lanes 3–6 and 7–9, respectively), HEG19 being a less potent activator than the full-length receptor (HEG0), as expected. PLZF has little if any effect on CAT activity (lanes 13–15). PLZF-ERα also does not activate the CAT reporter gene. Indeed some repression of the background CAT activity seen with pSG5 is observed (lanes 10–12, compare with lanes 1–3). Certainly no activation is seen with PLZF-ERα in the presence of 17β-oestradiol. These results indicate that PLZF-ERα is unable to activate expression of oestrogen responsive genes despite having an ability to bind to oestrogen response elements.

In order to investigate whether PLZF-ERα can inhibit transactivation by endogenous ER, we transiently transfected MCF-7 cells. This is a breast cancer-derived cell line that expresses the oestrogen receptor and requires oestrogen for growth. MCF-7 cells were transiently transfected with an oestrogen responsive reporter gene 17M-ERE-G-CAT and pCH110, together with pSG5 (lanes 1–3), HEG19 (lanes 4–6), PLZF-ERα (lanes 7–9) or PLZF (lanes 10–12) as described for COS-1 cells above. Ligands were added as appropriate (see FIG. 4B). The results are displayed in the form of a bar chart. The level of transactivation in the presence of E (FIG. 4B, lane 2) was taken as 100%. Transfection of PLZF-ERα reduced reporter gene activity due to the endogenous ER to below that seen in the absence of ligand (FIG. 4B, compare lanes 1 and 7). Addition of 17β-oestradiol (E, lane 8) or the partial antagonist 4-hydroxytamoxifen (O, lane 9) did not result in release from inhibition, suggesting that PLZF-ERα inhibits transactivation in a ligand-independent manner.

From Example 1 it can be concluded that the RARα portion of PLZF-RARα can be replaced by another related DNA binding protein activity.

PLZF-ERα protein retains the ability to bind specifically to the oestrogen receptor DNA binding element. PLZF-ERα displays little, if any ability to activate gene expression.

Replacing the RARα DNA binding activity redirects gene inactivation to the binding specificity of the new DNA binding domain.

PLZF-ERα is able to compete with endogenous ERα in a breast cancer cell lines to over-ride oestrogen-activated gene expression.

PLZF-ERα inhibits oestrogen responsive gene expression in an oestrogen-independent manner.

EXAMPLE 2

Construction of PLZF-AR Gene Fusion and its Use

A second analogue of the PLZF-RARα gene fusion was produced in which the RARα portion was replaced by an equivalent region of the human androgen receptor (AR). A 1146 bp region of a human AR cDNA clone (Tilley et al 1989 Proc. Natl. Acad. Sci. USA 86, 327–331) was amplified by PCR using primers which introduced an in frame XhoI site into the 5' coding region and a BamHI site immediately following the stop codon (Primers AR F1, ggagctcgagggT-TGGAGACTGCCAGGGACC (SEQ ID NO:4) and AR R1; gtgaggatccTCACTGGGTGTGGAAATAGATGG (SEQ ID NO:5)). The AR PCR product was restriction enzyme digested with XhoI and BanHI and ligated with XhoI/BanHI digested PLZF-ER to replace the ER portion with AR. The ligation product was used to transform E. coli bacteria and plasmid DNA prepared from individual clones. Recombinant pSG5 plasmids containing PLZF-AR gene fusion DNA were initially identified by restriction enzyme digestion and were subsequently confirmed by DNA sequence analysis. The resultant cloned PLZF-AR gene encodes the first 455 amino acids of PLZF, fused in frame with amino acids 537–917 of human AR. Transient transfections in COS-1 cells, followed by immunoblotting of cell extracts with antibodies directed against PLZF or AR were used to confirm expression and expected size.

FIG. 6 shows that PLZF-AR represses activation of an androgen-responsive reporter gene. COS-1 cells were co-transfected with 2 μg of the reporter gene pG29G-tk-CAT and 1 μg of the β-galactosidase reporter plasmid pSGΔlacZ together with 2 μg of the expression plasmid pSG5 (lanes 1–2), or 1 μg of pSG5 (lanes 34, 9–12), AR (lanes 3–8), PLZF-AR (lanes 5–6, 9–10) or PLZF (lanes 7–8, 11–12), as indicated, in the presence or absence of R1881 (1 nM), prepared in ethanol. R1881 was purchased from DuPont, USA. Ethanol was added to the control samples (–). The reporter gene has been described in Schule et al (1988) *Science* 242, 1418–1420.

From these experiments it can be concluded that the PLZF-androgen receptor fusion inhibits androgen receptor-mediated transcription activation.

EXAMPLE 3

Suppression of Androgen Receptor-Mediated Transcription in a Prostate Cancer Patient A plasmid vector is produced which encodes the PLZF-AR fusion protein as described in Example 2 under the control of the PSA gene promoter which allows for selective expression in prostate tissue. The plasmid is prepared in a sterile and pyrogen-free form and is formulated into liposomes. The plasmid DNA-containing liposomes are administered into the vicinity of the prostate. Plasmid DNA is taken up by the prostate cancer cells and androgen receptor-mediated transcription is suppressed selectively in prostate cells.

EXAMPLE 4

Suppression of Oestrogen Receptor-Mediated Transcription in a Breast Cancer Patient A retroviral vector is produced which encodes the PLZF-ER fusion protein as described in Example 1. The retroviral vector is administered into the site of the breast tumour. Retroviral RNA is taken up by the breast cancer cells and oestrogen receptor-mediated transcription is suppressed selectively in breast cells.

The invention claimed is:

1. An in vitro method of suppressing the expression of an androgen-responsive reporter gene in COS-1 cells, the method comprising introducing into the cell a polynucleotide encoding promyelocytic leukemia zinc finger-androgen receptor α (PLZF-ARα).

2. An in vitro method of suppressing the expression of an estrogen-responsive reporter gene in a breast cell, the method comprising introducing into the cell a polynucleotide encoding promyelocytic leukemia zinc finger-estrogen receptor α (PLZF-ERα).

3. The method according to claim 2 wherein the breast cell is a breast cancer cell.

4. The method according to claim 3 wherein the breast cancer cell is an MCF-7 cell.

* * * * *

SEQUENCE LISTING

```
<160> NUMBER OF SEQ ID NOS: 11

<210> SEQ ID NO 1
<211> LENGTH: 35
<212> TYPE: DNA
<213> ORGANISM: Artificial
<220> FEATURE:
<223> OTHER INFORMATION: Primer PLZF R

<400> SEQUENCE: 1
ccgctcgagc tgaatgagcc agtaagtgca ttctc                         35

<210> SEQ ID NO 2
<211> LENGTH: 30
<212> TYPE: DNA
<213> ORGANISM: Artificial
```

```
<220> FEATURE:
<223> OTHER INFORMATION: Primer ERF1

<400> SEQUENCE: 2
ccgctcgagg gccaaattca gataatcgac                                      30

<210> SEQ ID NO 3
<211> LENGTH: 25
<212> TYPE: DNA
<213> ORGANISM: Artificial
<220> FEATURE:
<223> OTHER INFORMATION: Primer ER R1

<400> SEQUENCE: 3
ccgtgtggga tccagggagc tctca                                           25

<210> SEQ ID NO 4
<211> LENGTH: 31
<212> TYPE: DNA
<213> ORGANISM: Artificial
<220> FEATURE:
<223> OTHER INFORMATION: Primer AR F1

<400> SEQUENCE: 4
ggagctcgag ggttggagac tgccagggac c                                    31

<210> SEQ ID NO 5
<211> LENGTH: 33
<212> TYPE: DNA
<213> ORGANISM: Artificial
<220> FEATURE:
<223> OTHER INFORMATION: Primer AR R1

<400> SEQUENCE: 5
gtgaggatcc tcactgggtg tggaaataga tgg                                  33

<210> SEQ ID NO 6
<211> LENGTH: 482
<212> TYPE: PRT
<213> ORGANISM: Homo sapiens

<400> SEQUENCE: 6
```

Met Ala Gln Thr Gln Gly Thr Arg Arg Lys Val Cys Tyr Tyr Tyr Asp
 1               5                  10                  15

Gly Asp Val Gly Asn Tyr Tyr Gly Gln Gly His Pro Met Lys Pro
             20                  25                  30

His Arg Ile Arg Met Thr His Asn Leu Leu Leu Asn Tyr Gly Leu Tyr
             35                  40                  45

Arg Lys Met Glu Ile Tyr Arg Pro His Lys Ala Asn Ala Glu Glu Met
     50                  55                  60

Thr Lys Tyr His Ser Asp Asp Tyr Ile Lys Phe Leu Arg Ser Ile Arg
 65                  70                  75                  80

Pro Asp Asn Met Ser Glu Tyr Ser Lys Gln Met Gln Arg Phe Asn Val
                 85                  90                  95

Gly Glu Asp Cys Pro Val Phe Asp Gly Leu Phe Glu Phe Cys Gln Leu
            100                 105                 110

Ser Thr Gly Gly Ser Val Ala Ser Ala Val Lys Leu Asn Lys Gln Gln
        115                 120                 125

Thr Asp Ile Ala Val Asn Trp Ala Gly Gly Leu His His Ala Lys Lys
    130                 135                 140

Ser Glu Ala Ser Gly Phe Cys Tyr Val Asn Asp Ile Val Leu Ala Ile

```
                145                 150                 155                 160
Leu Glu Leu Leu Lys Tyr His Gln Arg Val Leu Tyr Ile Asp Ile Asp
                    165                 170                 175
Ile His His Gly Asp Gly Val Glu Glu Ala Phe Tyr Thr Thr Asp Arg
                180                 185                 190
Val Met Thr Val Ser Phe His Lys Tyr Gly Glu Tyr Phe Pro Gly Thr
            195                 200                 205
Gly Asp Leu Arg Asp Ile Gly Ala Gly Lys Gly Lys Tyr Tyr Ala Val
        210                 215                 220
Asn Tyr Pro Leu Arg Asp Gly Ile Asp Asp Glu Ser Tyr Glu Ala Ile
225                 230                 235                 240
Phe Lys Pro Val Met Ser Lys Val Met Glu Met Phe Gln Pro Ser Ala
                245                 250                 255
Val Val Leu Gln Cys Gly Ser Asp Ser Leu Ser Gly Asp Arg Leu Gly
                260                 265                 270
Cys Phe Asn Leu Thr Ile Lys Gly His Ala Lys Cys Val Glu Phe Val
            275                 280                 285
Lys Ser Phe Asn Leu Pro Met Leu Met Leu Gly Gly Gly Gly Tyr Thr
        290                 295                 300
Ile Arg Asn Val Ala Arg Cys Trp Thr Tyr Glu Thr Ala Val Ala Leu
305                 310                 315                 320
Asp Thr Glu Ile Pro Asn Glu Leu Pro Tyr Asn Asp Tyr Phe Glu Tyr
                325                 330                 335
Phe Gly Pro Asp Phe Lys Leu His Ile Ser Pro Ser Asn Met Thr Asn
                340                 345                 350
Gln Asn Thr Asn Glu Tyr Leu Glu Lys Ile Lys Gln Arg Leu Phe Glu
            355                 360                 365
Asn Leu Arg Met Leu Pro His Ala Pro Gly Val Gln Met Gln Ala Ile
        370                 375                 380
Pro Glu Asp Ala Ile Pro Glu Glu Ser Gly Asp Glu Asp Glu Asp Asp
385                 390                 395                 400
Pro Asp Lys Arg Ile Ser Ile Cys Ser Ser Asp Lys Arg Ile Ala Cys
                405                 410                 415
Glu Glu Glu Phe Ser Asp Ser Glu Glu Gly Glu Gly Gly Arg Lys
                420                 425                 430
Asn Ser Ser Asn Phe Lys Lys Ala Lys Arg Val Lys Thr Glu Asp Glu
            435                 440                 445
Lys Glu Lys Asp Pro Glu Glu Lys Lys Glu Val Thr Glu Glu Glu Lys
        450                 455                 460
Thr Lys Glu Glu Lys Pro Glu Ala Lys Gly Val Lys Glu Glu Val Lys
465                 470                 475                 480
Leu Ala

<210> SEQ ID NO 7
<211> LENGTH: 501
<212> TYPE: PRT
<213> ORGANISM: Arabidopsis thaliana

<400> SEQUENCE: 7

Met Asp Thr Gly Gly Asn Ser Leu Ala Ser Gly Pro Asp Gly Val Lys
1               5                   10                  15
Arg Lys Val Cys Tyr Phe Tyr Asp Pro Glu Val Gly Asn Tyr Tyr Tyr
                20                  25                  30
Gly Gln Gly His Pro Met Lys Pro His Arg Ile Arg Met Thr His Ala
```

-continued

```
                35                  40                  45
Leu Leu Ala His Tyr Gly Leu Leu Gln His Met Gln Val Leu Lys Pro
 50                  55                  60

Phe Pro Ala Arg Asp Arg Asp Leu Cys Arg Phe His Ala Asp Asp Tyr
 65                  70                  75                  80

Val Ser Phe Leu Arg Ser Ile Thr Pro Glu Thr Gln Gln Asp Gln Ile
                 85                  90                  95

Arg Gln Leu Lys Arg Phe Asn Val Gly Glu Asp Cys Pro Val Phe Asp
                100                 105                 110

Gly Leu Tyr Ser Phe Cys Gln Thr Tyr Ala Gly Gly Ser Val Gly Gly
                115                 120                 125

Ser Val Lys Leu Asn His Gly Leu Cys Asp Ile Ala Ile Asn Trp Ala
130                 135                 140

Gly Gly Leu His His Ala Lys Lys Cys Glu Ala Ser Gly Phe Cys Tyr
145                 150                 155                 160

Val Asn Asp Ile Val Leu Ala Ile Leu Glu Leu Leu Lys Gln His Glu
                165                 170                 175

Arg Val Leu Tyr Val Asp Ile Asp Ile His His Gly Asp Gly Val Glu
                180                 185                 190

Glu Ala Phe Tyr Ala Thr Asp Arg Val Met Thr Val Ser Phe His Lys
                195                 200                 205

Phe Gly Asp Tyr Phe Pro Gly Thr Gly His Ile Gln Asp Ile Gly Tyr
210                 215                 220

Gly Ser Gly Lys Tyr Tyr Ser Leu Asn Val Pro Leu Asp Asp Gly Ile
225                 230                 235                 240

Asp Asp Glu Ser Tyr His Leu Leu Phe Lys Pro Ile Met Gly Lys Val
                245                 250                 255

Met Glu Ile Phe Arg Pro Gly Ala Val Val Leu Gln Cys Gly Ala Asp
                260                 265                 270

Ser Leu Ser Gly Asp Arg Leu Gly Cys Phe Asn Leu Ser Ile Lys Gly
                275                 280                 285

His Ala Glu Cys Val Lys Phe Met Arg Ser Phe Asn Val Pro Leu Leu
290                 295                 300

Leu Leu Gly Gly Gly Gly Tyr Thr Ile Arg Asn Val Ala Arg Cys Trp
305                 310                 315                 320

Cys Tyr Glu Thr Gly Val Ala Leu Gly Val Glu Val Glu Asp Lys Met
                325                 330                 335

Pro Glu His Glu Tyr Tyr Glu Tyr Phe Gly Pro Asp Tyr Thr Leu His
                340                 345                 350

Val Ala Pro Ser Asn Met Glu Asn Lys Asn Ser Arg Gln Met Leu Glu
                355                 360                 365

Glu Ile Arg Asn Asp Leu Leu His Asn Leu Ser Lys Leu Gln His Ala
                370                 375                 380

Pro Ser Val Pro Phe Gln Glu Arg Pro Pro Asp Thr Glu Thr Pro Glu
385                 390                 395                 400

Val Asp Glu Asp Gln Glu Asp Gly Asp Lys Arg Trp Asp Pro Asp Ser
                405                 410                 415

Asp Met Asp Val Asp Asp Arg Lys Pro Ile Pro Ser Arg Val Lys
                420                 425                 430

Arg Glu Ala Val Glu Pro Asp Thr Lys Asp Lys Asp Gly Leu Lys Gly
                435                 440                 445

Ile Met Glu Arg Gly Lys Gly Cys Glu Val Glu Val Asp Glu Ser Gly
450                 455                 460
```

-continued

Ser Thr Lys Val Thr Gly Val Asn Pro Val Gly Val Glu Glu Ala Ser
465                 470                 475                 480

Val Lys Met Glu Glu Glu Gly Thr Asn Lys Gly Gly Ala Glu Gln Ala
                485                 490                 495

Phe Pro Pro Lys Thr
            500

<210> SEQ ID NO 8
<211> LENGTH: 433
<212> TYPE: PRT
<213> ORGANISM: Saccharomyces cerevisiae

<400> SEQUENCE: 8

Met Val Tyr Glu Ala Thr Pro Phe Asp Pro Ile Thr Val Lys Pro Ser
1               5                   10                  15

Asp Lys Arg Arg Val Ala Tyr Phe Tyr Asp Ala Asp Val Gly Asn Tyr
                20                  25                  30

Ala Tyr Gly Ala Gly His Pro Met Lys Pro His Arg Ile Arg Met Ala
            35                  40                  45

His Ser Leu Ile Met Asn Tyr Gly Leu Tyr Lys Lys Met Glu Ile Tyr
50                  55                  60

Arg Ala Lys Pro Ala Thr Lys Gln Glu Met Cys Gln Phe His Thr Asp
65                  70                  75                  80

Glu Tyr Ile Asp Phe Leu Ser Arg Val Thr Pro Asp Asn Leu Glu Met
                85                  90                  95

Phe Lys Arg Glu Ser Val Lys Phe Asn Val Gly Asp Asp Cys Pro Val
            100                 105                 110

Phe Asp Gly Leu Tyr Glu Tyr Cys Ser Ile Ser Gly Gly Gly Ser Met
        115                 120                 125

Glu Gly Ala Ala Arg Leu Asn Arg Gly Lys Cys Asp Val Ala Val Asn
130                 135                 140

Tyr Ala Gly Gly Leu His His Ala Lys Lys Ser Glu Ala Ser Gly Phe
145                 150                 155                 160

Cys Tyr Leu Asn Asp Ile Val Leu Gly Ile Ile Glu Leu Leu Arg Tyr
                165                 170                 175

His Pro Arg Val Leu Tyr Ile Asp Ile Asp Val His His Gly Asp Gly
            180                 185                 190

Val Glu Glu Ala Phe Tyr Thr Thr Asp Arg Val Met Thr Cys Ser Phe
        195                 200                 205

His Lys Tyr Gly Glu Phe Phe Pro Gly Thr Gly Glu Leu Arg Asp Ile
    210                 215                 220

Gly Val Gly Ala Gly Lys Asn Tyr Ala Val Asn Val Pro Leu Arg Asp
225                 230                 235                 240

Gly Ile Asp Asp Ala Thr Tyr Arg Ser Val Phe Glu Pro Val Ile Lys
                245                 250                 255

Lys Ile Met Glu Trp Tyr Gln Pro Ser Ala Val Val Leu Gln Cys Gly
            260                 265                 270

Gly Asp Ser Leu Ser Gly Asp Arg Leu Gly Cys Phe Asn Leu Ser Met
        275                 280                 285

Glu Gly His Ala Asn Cys Val Asn Tyr Val Lys Ser Phe Gly Ile Pro
    290                 295                 300

Met Met Val Val Gly Gly Gly Gly Tyr Thr Met Arg Asn Val Ala Arg
305                 310                 315                 320

Thr Trp Cys Phe Glu Thr Gly Leu Leu Asn Asn Val Val Leu Asp Lys

-continued

```
                325                 330                 335
Asp Leu Pro Tyr Asn Glu Tyr Tyr Glu Tyr Tyr Gly Pro Asp Tyr Lys
            340                 345                 350
Leu Ser Val Arg Pro Ser Asn Met Phe Asn Val Asn Thr Pro Glu Tyr
            355                 360                 365
Leu Asp Lys Val Met Thr Asn Ile Phe Ala Asn Leu Glu Asn Thr Lys
            370                 375                 380
Tyr Ala Pro Ser Val Gln Leu Asn His Thr Pro Arg Asp Ala Glu Asp
385                 390                 395                 400
Leu Gly Asp Val Glu Glu Asp Ser Ala Glu Ala Lys Asp Thr Lys Gly
            405                 410                 415
Gly Ser Gln Tyr Ala Arg Asp Leu His Val Glu His Asp Asn Glu Phe
            420                 425                 430
Tyr

<210> SEQ ID NO 9
<211> LENGTH: 900
<212> TYPE: PRT
<213> ORGANISM: Artificial
<220> FEATURE:
<223> OTHER INFORMATION: Fusion protein PLZF-ER

<400> SEQUENCE: 9

Met Asp Leu Thr Lys Met Gly Met Ile Gln Leu Gln Asn Pro Ser His
1               5                   10                  15
Pro Thr Gly Leu Leu Cys Lys Ala Asn Gln Met Arg Leu Ala Gly Thr
            20                  25                  30
Leu Cys Asp Val Val Ile Met Val Asp Ser Gln Glu Phe His Ala His
            35                  40                  45
Arg Thr Val Leu Ala Cys Thr Ser Lys Met Phe Glu Ile Leu Phe His
            50                  55                  60
Arg Asn Ser Gln His Tyr Thr Leu Asp Phe Leu Ser Pro Lys Thr Phe
65                  70                  75                  80
Gln Gln Ile Leu Glu Tyr Ala Tyr Thr Ala Thr Leu Gln Ala Lys Ala
                85                  90                  95
Glu Asp Leu Asp Asp Leu Leu Tyr Ala Ala Glu Ile Leu Glu Ile Glu
            100                 105                 110
Tyr Leu Glu Glu Gln Cys Leu Lys Met Leu Glu Thr Ile Gln Ala Ser
            115                 120                 125
Asp Asp Asn Asp Thr Glu Ala Thr Met Ala Asp Gly Gly Ala Glu Glu
            130                 135                 140
Glu Glu Asp Arg Lys Ala Arg Tyr Leu Lys Asn Ile Phe Ile Ser Lys
145                 150                 155                 160
His Ser Ser Glu Glu Ser Gly Tyr Ala Ser Val Ala Gly Gln Ser Leu
                165                 170                 175
Pro Gly Pro Met Val Asp Gln Ser Pro Ser Val Ser Thr Ser Phe Gly
            180                 185                 190
Leu Ser Ala Met Ser Pro Thr Lys Ala Ala Val Asp Ser Leu Met Thr
            195                 200                 205
Ile Gly Gln Ser Leu Leu Gln Gly Thr Leu Gln Pro Pro Ala Gly Pro
            210                 215                 220
Glu Glu Pro Thr Leu Ala Gly Gly Arg His Pro Gly Val Ala Glu
225                 230                 235                 240
Val Lys Thr Glu Met Met Gln Val Asp Glu Val Pro Ser Gln Asp Ser
                245                 250                 255
```

-continued

```
Pro Gly Ala Ala Glu Ser Ser Ile Ser Gly Gly Met Gly Asp Lys Val
            260                 265                 270
Glu Glu Arg Gly Lys Glu Gly Pro Gly Thr Pro Thr Arg Ser Ser Val
            275                 280                 285
Ile Thr Ser Ala Arg Glu Leu His Tyr Gly Arg Glu Glu Ser Ala Glu
            290                 295                 300
Gln Val Pro Pro Pro Ala Glu Ala Gly Gln Ala Pro Thr Gly Arg Pro
305                 310                 315                 320
Glu His Pro Ala Pro Pro Glu Lys His Leu Gly Ile Tyr Ser Val
                325                 330                 335
Leu Pro Asn His Lys Ala Asp Ala Val Leu Ser Met Pro Ser Ser Val
                340                 345                 350
Thr Ser Gly Leu His Val Gln Pro Ala Leu Ala Val Ser Met Asp Phe
            355                 360                 365
Ser Thr Tyr Gly Gly Leu Leu Pro Gln Gly Phe Ile Gln Arg Glu Leu
            370                 375                 380
Phe Ser Lys Leu Gly Glu Leu Ala Val Gly Met Lys Ser Glu Ser Arg
385                 390                 395                 400
Thr Ile Gly Glu Gln Cys Ser Val Cys Gly Val Glu Leu Pro Asp Asn
                405                 410                 415
Glu Ala Val Glu Gln His Arg Lys Leu His Ser Gly Met Lys Thr Tyr
                420                 425                 430
Gly Cys Glu Leu Cys Gly Lys Arg Phe Leu Asp Ser Leu Arg Leu Arg
            435                 440                 445
Met His Leu Leu Ala His Ser Arg Pro Asn Ser Asp Asn Arg Arg Gln
450                 455                 460
Gly Gly Arg Glu Arg Leu Ala Ser Thr Asn Asp Lys Gly Ser Met Ala
465                 470                 475                 480
Met Glu Ser Ala Lys Glu Thr Arg Tyr Cys Ala Val Cys Asn Asp Tyr
                485                 490                 495
Ala Ser Gly Tyr His Tyr Gly Val Trp Ser Cys Glu Gly Cys Lys Ala
            500                 505                 510
Phe Phe Lys Arg Ser Ile Gln Gly His Asn Asp Tyr Met Cys Pro Ala
            515                 520                 525
Thr Asn Gln Cys Thr Ile Asp Lys Asn Arg Arg Lys Ser Cys Gln Ala
            530                 535                 540
Cys Arg Leu Arg Lys Cys Tyr Glu Val Gly Met Met Lys Gly Gly Ile
545                 550                 555                 560
Arg Lys Asp Arg Arg Gly Gly Arg Met Leu Lys His Lys Arg Gln Arg
                565                 570                 575
Asp Asp Gly Glu Gly Arg Gly Glu Val Gly Ser Ala Gly Asp Met Arg
            580                 585                 590
Ala Ala Asn Leu Trp Pro Ser Pro Leu Met Ile Lys Arg Ser Lys Lys
            595                 600                 605
Asn Ser Leu Ala Leu Ser Leu Thr Ala Asp Gln Met Val Ser Ala Leu
            610                 615                 620
Leu Asp Ala Glu Pro Pro Ile Leu Tyr Ser Glu Tyr Asp Pro Thr Arg
625                 630                 635                 640
Pro Phe Ser Glu Ala Ser Met Met Gly Leu Leu Thr Asn Leu Ala Asp
                645                 650                 655
Arg Glu Leu Val His Met Ile Asn Trp Ala Lys Arg Val Pro Gly Phe
                660                 665                 670
```

```
Val Asp Leu Thr Leu His Asp Gln Val His Leu Leu Glu Cys Ala Trp
        675                 680                 685

Leu Glu Ile Leu Met Ile Gly Leu Val Trp Arg Ser Met Glu His Pro
        690                 695                 700

Val Lys Leu Leu Phe Ala Pro Asn Leu Leu Asp Arg Asn Gln Gly
705                 710                 715                 720

Lys Cys Val Glu Gly Met Val Glu Ile Phe Asp Met Leu Leu Ala Thr
                    725                 730                 735

Ser Ser Arg Phe Arg Met Met Asn Leu Gln Gly Glu Glu Phe Val Cys
            740                 745                 750

Leu Lys Ser Ile Ile Leu Leu Asn Ser Gly Val Tyr Thr Phe Leu Ser
            755                 760                 765

Ser Thr Leu Lys Ser Leu Glu Glu Lys Asp His Ile His Arg Val Leu
    770                 775                 780

Asp Lys Ile Thr Asp Thr Leu Ile His Leu Met Ala Lys Ala Gly Leu
785                 790                 795                 800

Thr Leu Gln Gln Gln His Gln Arg Leu Ala Gln Leu Leu Leu Ile Leu
                805                 810                 815

Ser His Ile Arg His Met Ser Asn Lys Gly Met Glu His Leu Tyr Ser
            820                 825                 830

Met Lys Cys Lys Asn Val Val Pro Leu Tyr Asp Leu Leu Leu Glu Met
            835                 840                 845

Leu Asp Ala His Arg Leu His Ala Pro Thr Ser Arg Gly Gly Ala Ser
    850                 855                 860

Val Glu Glu Thr Asp Gln Ser His Leu Ala Thr Ala Gly Ser Thr Ser
865                 870                 875                 880

Ser His Ser Leu Gln Lys Tyr Tyr Ile Thr Gly Glu Ala Glu Gly Phe
                885                 890                 895

Pro Ala Thr Val
            900

<210> SEQ ID NO 10
<211> LENGTH: 416
<212> TYPE: PRT
<213> ORGANISM: Artificial
<220> FEATURE:
<223> OTHER INFORMATION: Amino acids 180 to 595 of human ERalpha

<400> SEQUENCE: 10

Lys Glu Thr Arg Tyr Cys Ala Val Cys Asn Asp Tyr Ala Ser Gly Tyr
1               5                   10                  15

His Tyr Gly Val Trp Ser Cys Glu Gly Cys Lys Ala Phe Phe Lys Arg
                20                  25                  30

Ser Ile Gln Gly His Asn Asp Tyr Met Cys Pro Ala Thr Asn Gln Cys
            35                  40                  45

Thr Ile Asp Lys Asn Arg Arg Lys Ser Cys Gln Ala Cys Arg Leu Arg
        50                  55                  60

Lys Cys Tyr Glu Val Gly Met Met Lys Gly Gly Ile Arg Lys Asp Arg
65                  70                  75                  80

Arg Gly Gly Arg Met Leu Lys His Lys Arg Gln Arg Asp Asp Gly Glu
                85                  90                  95

Gly Arg Gly Glu Val Gly Ser Ala Gly Asp Met Arg Ala Ala Asn Leu
            100                 105                 110

Trp Pro Ser Pro Leu Met Ile Lys Arg Ser Lys Lys Asn Ser Leu Ala
        115                 120                 125
```

```
Leu Ser Leu Thr Ala Asp Gln Met Val Ser Ala Leu Leu Asp Ala Glu
    130                 135                 140
Pro Pro Ile Leu Tyr Ser Glu Tyr Asp Pro Thr Arg Pro Phe Ser Glu
145                 150                 155                 160
Ala Ser Met Met Gly Leu Leu Thr Asn Leu Ala Asp Arg Glu Leu Val
                165                 170                 175
His Met Ile Asn Trp Ala Lys Arg Val Pro Gly Phe Val Asp Leu Thr
            180                 185                 190
Leu His Asp Gln Val His Leu Leu Glu Cys Ala Trp Leu Glu Ile Leu
        195                 200                 205
Met Ile Gly Leu Val Trp Arg Ser Met Glu His Pro Val Lys Leu Leu
    210                 215                 220
Phe Ala Pro Asn Leu Leu Leu Asp Arg Asn Gln Gly Lys Cys Val Glu
225                 230                 235                 240
Gly Met Val Glu Ile Phe Asp Met Leu Leu Ala Thr Ser Ser Arg Phe
                245                 250                 255
Arg Met Met Asn Leu Gln Gly Glu Glu Phe Val Cys Leu Lys Ser Ile
            260                 265                 270
Ile Leu Leu Asn Ser Gly Val Tyr Thr Phe Leu Ser Ser Thr Leu Lys
        275                 280                 285
Ser Leu Glu Glu Lys Asp His Ile His Arg Val Leu Asp Lys Ile Thr
    290                 295                 300
Asp Thr Leu Ile His Leu Met Ala Lys Ala Gly Leu Thr Leu Gln Gln
305                 310                 315                 320
Gln His Gln Arg Leu Ala Gln Leu Leu Leu Ile Leu Ser His Ile Arg
                325                 330                 335
His Met Ser Asn Lys Gly Met Glu His Leu Tyr Ser Met Lys Cys Lys
            340                 345                 350
Asn Val Val Pro Leu Tyr Asp Leu Leu Leu Glu Met Leu Asp Ala His
        355                 360                 365
Arg Leu His Ala Pro Thr Ser Arg Gly Gly Ala Ser Val Glu Glu Thr
    370                 375                 380
Asp Gln Ser His Leu Ala Thr Ala Gly Ser Thr Ser Ser His Ser Leu
385                 390                 395                 400
Gln Lys Tyr Tyr Ile Thr Gly Glu Ala Glu Gly Phe Pro Ala Thr Val
                405                 410                 415

<210> SEQ ID NO 11
<211> LENGTH: 836
<212> TYPE: PRT
<213> ORGANISM: Artificial
<220> FEATURE:
<223> OTHER INFORMATION: Fusion between PLZF and AR

<400> SEQUENCE: 11

Met Asp Leu Thr Lys Met Gly Met Ile Gln Leu Gln Asn Pro Ser His
1               5                   10                  15
Pro Thr Gly Leu Leu Cys Lys Ala Asn Gln Met Arg Leu Ala Gly Thr
                20                  25                  30
Leu Cys Asp Val Val Ile Met Val Asp Ser Gln Glu Phe His Ala His
            35                  40                  45
Arg Thr Val Leu Ala Cys Thr Ser Lys Met Phe Glu Ile Leu Phe His
        50                  55                  60
Arg Asn Ser Gln His Tyr Thr Leu Asp Phe Leu Ser Pro Lys Thr Phe
65                  70                  75                  80
```

-continued

```
Gln Gln Ile Leu Glu Tyr Ala Tyr Thr Ala Thr Leu Gln Ala Lys Ala
            85                  90                  95
Glu Asp Leu Asp Asp Leu Leu Tyr Ala Ala Glu Ile Leu Glu Ile Glu
            100                 105                 110
Tyr Leu Glu Glu Gln Cys Leu Lys Met Leu Glu Thr Ile Gln Ala Ser
            115                 120                 125
Asp Asp Asn Asp Thr Glu Ala Thr Met Ala Asp Gly Gly Ala Glu Glu
        130                 135                 140
Glu Glu Asp Arg Lys Ala Arg Tyr Leu Lys Asn Ile Phe Ile Ser Lys
145                 150                 155                 160
His Ser Ser Glu Glu Ser Gly Tyr Ala Ser Val Ala Gly Gln Ser Leu
                165                 170                 175
Pro Gly Pro Met Val Asp Gln Ser Pro Ser Val Ser Thr Ser Phe Gly
            180                 185                 190
Leu Ser Ala Met Ser Pro Thr Lys Ala Ala Val Asp Ser Leu Met Thr
            195                 200                 205
Ile Gly Gln Ser Leu Leu Gln Gly Thr Leu Gln Pro Pro Ala Gly Pro
    210                 215                 220
Glu Glu Pro Thr Leu Ala Gly Gly Arg His Pro Gly Val Ala Glu
225                 230                 235                 240
Val Lys Thr Glu Met Met Gln Val Asp Glu Val Pro Ser Gln Asp Ser
                245                 250                 255
Pro Gly Ala Ala Glu Ser Ser Ile Ser Gly Gly Met Gly Asp Lys Val
            260                 265                 270
Glu Glu Arg Gly Lys Glu Gly Pro Gly Thr Pro Thr Arg Ser Ser Val
            275                 280                 285
Ile Thr Ser Ala Arg Glu Leu His Tyr Gly Arg Glu Glu Ser Ala Glu
    290                 295                 300
Gln Val Pro Pro Pro Ala Glu Ala Gly Gln Ala Pro Thr Gly Arg Pro
305                 310                 315                 320
Glu His Pro Ala Pro Pro Glu Lys His Leu Gly Ile Tyr Ser Val
                325                 330                 335
Leu Pro Asn His Lys Ala Asp Ala Val Leu Ser Met Pro Ser Ser Val
            340                 345                 350
Thr Ser Gly Leu His Val Gln Pro Ala Leu Ala Val Ser Met Asp Phe
            355                 360                 365
Ser Thr Tyr Gly Gly Leu Leu Pro Gln Gly Phe Ile Gln Arg Glu Leu
    370                 375                 380
Phe Ser Lys Leu Gly Glu Leu Ala Val Gly Met Lys Ser Glu Ser Arg
385                 390                 395                 400
Thr Ile Gly Glu Gln Cys Ser Val Cys Gly Val Glu Leu Pro Asp Asn
                405                 410                 415
Glu Ala Val Glu Gln His Arg Lys Leu His Ser Gly Met Lys Thr Tyr
            420                 425                 430
Gly Cys Glu Leu Cys Gly Lys Arg Phe Leu Asp Ser Leu Arg Leu Arg
            435                 440                 445
Met His Leu Leu Ala His Ser Asp Met Arg Leu Glu Thr Ala Arg Asp
    450                 455                 460
His Val Leu Pro Ile Asp Tyr Tyr Phe Pro Pro Gln Lys Thr Cys Leu
465                 470                 475                 480
Ile Cys Gly Asp Glu Ala Ser Gly Cys His Tyr Gly Ala Leu Thr Cys
                485                 490                 495
Gly Ser Cys Lys Val Phe Phe Lys Arg Ala Ala Glu Gly Lys Gln Lys
```

-continued

```
                     500                 505                 510
     Tyr Leu Cys Ala Ser Arg Asn Asp Cys Thr Ile Asp Lys Phe Arg Arg
                 515                 520                 525
     Lys Asn Cys Pro Ser Cys Arg Leu Arg Lys Cys Tyr Glu Ala Gly Met
                 530                 535                 540
     Thr Leu Gly Ala Arg Lys Leu Lys Lys Leu Gly Asn Leu Lys Leu Gln
     545                 550                 555                 560
     Glu Glu Gly Glu Ala Ser Ser Thr Thr Ser Pro Thr Glu Thr Thr
                         565                 570                 575
     Gln Lys Leu Thr Val Ser His Ile Glu Gly Tyr Glu Cys Gln Pro Ile
                     580                 585                 590
     Phe Leu Asn Val Leu Glu Ala Ile Glu Pro Gly Val Val Cys Ala Gly
                 595                 600                 605
     His Asp Asn Asn Gln Pro Asp Ser Phe Ala Ala Leu Leu Ser Ser Leu
                 610                 615                 620
     Asn Glu Leu Gly Glu Arg Gln Leu Val His Val Val Lys Trp Ala Lys
     625                 630                 635                 640
     Ala Leu Pro Gly Phe Arg Asn Leu His Val Asp Asp Gln Met Ala Val
                         645                 650                 655
     Ile Gln Tyr Ser Trp Met Gly Leu Met Val Phe Ala Met Gly Trp Arg
                     660                 665                 670
     Ser Phe Thr Asn Val Asn Ser Arg Met Leu Tyr Phe Ala Pro Asp Leu
                 675                 680                 685
     Val Phe Asn Glu Tyr Arg Met His Lys Ser Arg Met Tyr Ser Gln Cys
                 690                 695                 700
     Val Arg Met Arg His Leu Ser Gln Glu Phe Gly Trp Leu Gln Ile Thr
     705                 710                 715                 720
     Pro Gln Glu Phe Leu Cys Met Lys Ala Leu Leu Leu Phe Ser Ile Ile
                         725                 730                 735
     Pro Val Asp Gly Leu Lys Asn Gln Lys Phe Phe Asp Glu Leu Arg Met
                     740                 745                 750
     Asn Tyr Ile Lys Glu Leu Asp Arg Ile Ile Ala Cys Lys Arg Lys Asn
                 755                 760                 765
     Pro Thr Ser Cys Ser Arg Arg Phe Tyr Gln Leu Thr Lys Leu Leu Asp
                 770                 775                 780
     Ser Val Gln Pro Ile Ala Arg Glu Leu His Gln Phe Thr Phe Asp Leu
     785                 790                 795                 800
     Leu Ile Lys Ser His Met Val Ser Val Asp Phe Pro Glu Met Met Ala
                         805                 810                 815
     Glu Ile Ile Ser Val Gln Val Pro Lys Ile Leu Ser Gly Lys Val Lys
                     820                 825                 830
     Pro Ile Tyr Phe
                 835
```